US008143423B2

(12) United States Patent
Zhang et al.

(10) Patent No.: US 8,143,423 B2
(45) Date of Patent: Mar. 27, 2012

(54) N-HETEROCYCLIC CARBENE (NHC) CATALYZED SYNTHESIS OF HYDROXAMIC ACIDS

(75) Inventors: Yugen Zhang, Sinagapore (SG); Jackie Y. Ying, Singapore (SG); Jayasree Seayad, Singapore (SG); Fong Tian Wong, Singapore (SG); Pranab K. Patra, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 12/532,613

(22) PCT Filed: Mar. 20, 2008

(86) PCT No.: PCT/SG2008/000087
§ 371 (c)(1),
(2), (4) Date: Sep. 22, 2009

(87) PCT Pub. No.: WO2008/115153
PCT Pub. Date: Sep. 25, 2008

(65) Prior Publication Data
US 2010/0105921 A1      Apr. 29, 2010

Related U.S. Application Data

(60) Provisional application No. 60/907,133, filed on Mar. 22, 2007, provisional application No. 61/006,771, filed on Jan. 30, 2008.

(51) Int. Cl.
*C07C 259/10* (2006.01)
*C07C 259/06* (2006.01)
*C07C 259/04* (2006.01)
*C07C 259/08* (2006.01)
*C07D 233/90* (2006.01)

(52) U.S. Cl. .................... 548/333.5; 560/312; 562/621; 562/622

(58) Field of Classification Search ........................ None
See application file for complete search history.

(56) References Cited

FOREIGN PATENT DOCUMENTS
WO    WO 2008/115149 A1    9/2008

OTHER PUBLICATIONS

European Office Action issued from corresponding EP application 08724351.5, Oct. 28, 2010, 4 pages.
Aires-De-Sousa, J., et al., *Tetrahedron: Asym.* 2001, p. 3349-3365, vol. No. 12.
Armour, C. A.; Ryan, D. E., *Can. J. Chem.* 1957, p. 1454-1460, vol. No. 35.
Bode, J. W.; Sohn, S. S., *J. Am. Chem. Soc.* 2007, p. 13798-13799, vol. No. 129.
Boukhris, S., et al., *Tetrahedron Lett.* 1996, p. 179-182, vol. No. 37.
Breslow, R., *J. Am. Chem. Soc.* 1958, p. 3719-3726, vol. No. 80.
Burstein, C., et al., *Synthesis* 2006, p. 2418-2439.
Burstein, C.; Glorius, F., *Angew. Chem., Int. Ed.* 2004, p. 6205-6208, vol. No. 43.
Chan, A.; Scheidt, K. A., *Org. Lett.* 2005, p. 905-908, vol. No. 7.
Chatterjee, B., *Coord. Chem. Rev.* 1978, p. 281-303, vol. No. 26.
Chow, K. Y. —K.; Bode, J. W., *J. Am. Chem. Soc.* 2004, p. 8126-8127, vol. No. 126.
Corbett, M. D., et al., *J. Chem. Soc. Perkin Trans. I* 1983, p. 765-769.
Corbett, M. D., et al., *J. Chem. Soc. Perkin Trans. I* 1982, p. 345-350.
Enders, D., et al., *Chem. Rev.* 2007, p. 5606-5655, vol. No. 107.
Enders, D.; Balensiefer, T., *Acc. Chem. Res.* 2004, p. 534-541, vol. No. 37.
Enders, D.; Kallfass, U., *Angew. Chem., Int. Ed.* 2002, p. 1743-1745, vol. No. 41.
Enders, D., et al., *Angew. Chem., Int. Ed.* 2006, p. 1463-1467, vol. No. 45.
Fazary, A. E., et al., *Med. J. Islamic Acad. Sc.* 2001, p. 109-116, vol. No. 14.
Giacomelli, G., et al., *Org. Lett.* 2003, p. 2715-2717, vol. No. 5.
Hanna, P. E.; Banks, R. B., *Bioactivation of Foreign Compounds*; Anders, M. W., Ed., 1985, p. 375-402, Academic Press, New York.
He, M., et al., *J. Am. Chem. Soc.* 2006, p. 8418-8420, vol. No. 128.
Hirrlinger, B.; Stolz, A., *App. Env. Microbio.* 1997, p. 3390-3393.
Ho, C. Y., et al., *J. Org. Chem.* 2005, p. 4873-4875, vol. No. 70.
Hoshino, Y.; Yamamoto, Y., *J. Am. Chem. Soc.* 2000, p. 10452-10453, vol. No. 122.
Jung, M., *Curr. Med. Chem.* 2001, p. 1505-1511, vol. No. 8.
Kerr, M. S., et al., *J. Am. Chem. Soc.* 2000, p. 10298-10299, vol. No. 124.
Kerr, M. S., et al., *J. Org. Chem.* 2005, p. 5725-5728, vol. No. 70.
Kerr, M. S.; Rovis, T., *J. Am. Chem. Soc.* 2004, p. 8876-8877, vol. No. 126.
Kerr, M. S.; Rovis, T., *Synlett* 2003, p. 1934-1936.
Loverek, M., et al., *Croatica Chemica Acta*, 2000, p. 715-731, vol. No. 73.
Maehr, H., *Pure Appl. Chem.* 1971, p. 603-636, vol. No. 28.
Malkov, A. V., et al., *Org. Biomol. Chem.* 2005, p. 3194-3200, vol. 3.
Matlin, S. A., et al., *J. Chem. Soc. Perkin Trans. I* 1979, p. 2481-2487.
Marion, N., et al., *Angew. Chem., Int. Ed.* 2007, p. 2988-3000, vol. No. 46.
Miller, M. J., *Chem. Rev.* 1989, p. 1563-1579, vol. No. 89.
Momiyama, N., et al., *J. Am. Chem. Soc.* 2007, p. 1190-1195, vol. No. 129.
Nair, V., et al., *J. Am. Chem. Soc.* 2006, p. 8736-8737, vol. No. 128.
Pereira, M. M., et al., *J. Chem. Soc. Chem. Commun.* 1993, p. 38-40.
Porcheddu, A.; Giacomelli, G., *J. Org. Chem.* 2006, p. 7057-7059, vol. No. 71.
Reynolds, N. T.; Rovis, T., *J. Am. Chem. Soc.* 2005, 127, p. 16406-16407, vol. No. 127.
Reynolds, N. T., et al., *J. Am. Chem. Soc.* 2004, p. 9518-9519, vol. No. 126.
Sakamoto, Y., et al., *J. Org. Chem.* 1989, p. 4449-4453, vol. No. 54.
Schut, H. A. J.; Castonguay, A., *Drug Metab. Rev.* 1984, p. 753-839, vol. No. 15.
Seayad, J., et al., *Org. Lett.* 2008, p. 953-956, vol. No. 10.
Sohn, S. S.; Bode, J. W., *Org. Lett.* 2005, p. 3873-3876, vol. No. 7.
Sohn, S. S., et al., *J. Am. Chem. Soc.* 2004, p. 14370-14371, vol. No. 126.
Traber, B., et al., *Bull. Korean Chem. Soc.* 2001, p. 547-548, vol. No. 22.
Vora, H. U.; Rovis, T., *J. Am. Chem. Soc.* 2007, p. 13796-13797, vol. No. 129.

(Continued)

*Primary Examiner* — Sun Jae Loewe
(74) *Attorney, Agent, or Firm* — Klarquist Sparkman, LLP

(57) ABSTRACT

A process for preparing hydroxamic acids is provided. The process comprises reacting an aldehyde with a nitroso compound in the presence of a N-heterocyclic carbene (NHC) catalyst.

20 Claims, No Drawings

OTHER PUBLICATIONS

Yamamoto, H.; Momiyama, N., *Chem. Commun.* 2005, p. 3514-3525.
Momiyama, N.; Yamamoto, H., *J. Am. Chem. Soc.* 2005, p. 1080-1081, vol. No. 127.
Zeitler, K., *Angew. Chem., Int. Ed.* 2005, p. 7506-7510, vol. No. 44.
Zeitler, K., *Org. Lett.* 2006, p. 637-640, vol. No. 8.
Zuman, P.; Shah, B., *Chem. Rev.* 1994, p. 1621-1641, vol. No. 94.
Wong, F. T., et al., *Org. Lett.* 2008, p. 2333-2336, vol. No. 10.
Döbler, C., et al., *J. Am. Chem. Soc.* 2000, 122, 10289-10297.
International Search Report and Written Opinion for PCT/SG2008/000087.
Taichi Kano et al. Direct Asymmetric Hydroxyamination Reaction Catalyzed by an Axiall Chiral Secondary Amine Catalyst. *J. Am. Chem. Soc.* 2006, 128, 6046-6047.
Olga Kronja et al. Reaction of Substituted Nitrosobenzenes with Formaldehyde. *J. Chem. Soc. Chem. Commun.*, 1987, pp. 463-464.
Otto Neunhoeffer et al. Gemeinsame Disproportionierung von Nitrosoverbindungen und Aldehyden unter der Einwirkung von Alminiumalkoholat. Chemische Berichte, vol. 94, 1961, pp. 623-627, XP002574086.
Supplementary European Search Report (Application No. 08724351.5).

N-HETEROCYCLIC CARBENE (NHC) CATALYZED SYNTHESIS OF HYDROXAMIC ACIDS

This application claims the benefit of, and priority from, U.S. Provisional Patent Application Ser. No. 60/907,133, filed Mar. 22, 2007, and U.S. Provisional Patent Application Ser. No. 61/006,771, filed Jan. 30, 2008, which are both incorporated herein by reference.

This invention relates to a process for preparing a hydroxamic acid comprising reacting an aldehyde with a nitroso compound in the presence of a N-heterocyclic carbene (NHC) catalyst.

BACKGROUND

Hydroxamic acids play a number of roles in a range of biological and biochemical processes and systems. Accordingly, hydroxamic acids have been and continue to be investigated and their chemistry and biochemistry are well documented. Hydroxamic acids have been reported to act in a number of different capacities, including as antibacterial, antifungal and anticancer agents, and as specific enzyme inhibitors. Use of hydroxamic acids as metal ion chelators has been reported. A number of groups have reported on the investigation of hydroxamic acids in human clinical trials as drugs for the treatment of several diseases.

Pathways for synthesizing hydroxamic acids are of interest due to their pharmacological, toxicological and pathological properties. Approaches for synthesizing hydroxamic acids have been reported, including reactions involving the acylation of hydroxylamines. Other pathways for synthesizing hydroxamic acids have been reported, including reactions involving the oxidation of arylacylamides.

Preparation of Hydroxamic Acids Involving the reaction of nitroso compounds has been reported. Nitroso compounds have been reported as exhibiting a high reactivity of the nitroso group. The polarization of the nitrogen-oxygen bond, resembling that of the carbon-oxygen bond in a carbonyl group, results in susceptibility of the nitroso group to the addition of nucleophiles. Preparation of N-arylhydroxamic acids involving the reaction of aromatic nitroso compounds with oxoacids in the presence of acidic media has been reported. The conversion of aromatic nitroso compounds into hydroxamic acids using thiamine-dependent enzymes, such as α-ketoglutarate dehydrogenase, pyruvate decarboxylase and transketolase, has been reported (see, for example, Corbett, M. D.; Corbett, B. R.; Doerge, D. R. *J. Chem. Soc. Perkin Trans.* 1 1982, 345 and references therein; and Corbett, M. D.; Doerge, D. R.; Corbett, B. R. *J. Chem. Soc. Perkin Trans.* 1 1983, 765).

Many groups have reported that organocatalytic reactions provide an efficient means for metal-free carbon-nitrogen (C—N) bond and carbon-carbon (C—C) bond formation.

Examples of organocatalytic C—N bond formation reactions, including N-nitroso aldol reaction of enamines selectively forming N-hydroxyaminoketones, have been reported (see, for example, Yamamoto, H. and Momiyama N. *J. Am. Chem. Soc.* 2005, 127; 1080; and Momiyama, N.; Yamamoto, Y.; Yamamoto, H. *J. Am. Chem. Soc.* 2007, 129, 1190).

Many groups have repotted that N-heterocyclic carbene catalysts can be used for metal-free C—C bond formation via the nucleophilic "Breslow intermediate", or the homoenolate equivalent species. Depending on the electrophile, different types of reactions are possible via both intermediates.

Examples of the former path have been reported, including benzoin condensation, wherein an aryl aldehyde acts as the electrophile, and the Stetter reaction, wherein a Michael accepter acts as the electrophile. Other examples of this path have been reported, including redox reactions of α-functionalized aldehydes to form the corresponding esters or amides.

Examples of C—C bond forming reactions involving the homoenolate equivalent species have been reported, including lactonization, cyclopentannulation, and azannulation.

Approaches for the preparation of hydroxamic acids using readily available reactants and catalysts are desired.

SUMMARY

In one broad aspect of the present invention, there is provided a process for preparing a hydroxamic acid comprising reacting an aldehyde with a nitroso compound in the presence of a NHC catalyst.

In another broad aspect of the present invention, there is provided a process for preparing a chiral hydroxamic acid comprising reacting a α-branched aldehyde with a nitroso compound in the presence of an achiral NHC catalyst.

In a further broad aspect of the present invention, there is provided a process for preparing a chiral hydroxamic acid comprising reacting a α-branched aldehyde with a nitroso compound in the presence of a chiral NHC catalyst.

In still another aspect of the present invention, there is provided a process for preparing N-propionyloxy-N-phenylacrylamide.

DETAILED DESCRIPTION

I. Process for Preparing Hydroxamic Acid

In an embodiment of the present invention, an aldehyde may be reacted with a nitroso compound in the presence of a NHC catalyst to prepare a hydroxamic acid.

A. Aldehyde

The aldehyde which may be used in the present invention is not particularly limited. In an embodiment of the present invention, the aldehyde may be, for example, and without limitation, an alkyl, alkenyl, alkynyl, cycloalkyl, cycloalkenyl, aryl, arylalkyl, arylalkenyl, arylalkynyl or heterocyclic aldehyde which may be substituted with one or more substituents which are the same or different.

In an embodiment of the present invention, the aldehyde may be, for example, and without limitation, a compound represented by the formula (II):

wherein $R_1$ may be, for example, and without limitation, a hydrogen atom, a $C_{1-8}$ alkyl group which may be substituted with one or more substituents which are the same or different, a $C_{2-6}$ alkenyl group which may be substituted with one or more substituents which are the same or different, a $C_{2-6}$ alkynyl group which may be substituted with one or more substituents which are the same or different, a $C_{3-8}$ cycloalkyl group which may be substituted with one or more substituents which are the same or different, a $C_{3-8}$ cycloalkenyl group which may be substituted with one or more substituents which are the same or different, a $C_{6-14}$ aryl group which may be substituted with one or more substituents which are the same or different, a $C_{6-14}$ aryl-$C_{1-6}$ alkyl group which may be substituted with one or more substituents which are the same or different, a $C_{6-14}$ aryl-$C_{2-6}$ alkenyl group which may be substituted with one or more substituents which are the same or different, a $C_{6-14}$ aryl-$C_{2-6}$ alkynyl group which may be substituted with one or more substituents which are the same or different, a 4- to 10-membered non-aromatic heterocyclic group containing one or more heteroatoms which are independently nitrogen, sulfur or oxygen and which group may be substituted with one or more substituents which are the same or different, or a 5- to 14-membered aromatic heterocyclic group containing one or more heteroatoms which are independently nitrogen, sulfur or oxygen and which group may be substituted with one or more substituents which are the same or different.

The following definitions of the various groups as described herein are the same for all occurrences of these groups throughout the entire specification unless otherwise indicated.

The $C_{1-6}$ alkyl group of the alkyl containing groups which may be substituted, may be, for example, and without limitation, any straight or branched alkyl, for example, methyl, ethyl, n-propyl, i-propyl, sec-propyl, n-butyl, i-butyl, sec-butyl, t-butyl, n-pentyl, i-pentyl, sec-pentyl, t-pentyl, n-hexyl, i-hexyl, 1,2-dimethylpropyl, 2-ethylpropyl, 1-methyl-2-ethylpropyl, 1-ethyl-2-methylpropyl, 1,1,2-trimethylpropyl, 1,1,2-triethylpropyl, 1,1-dimethylbutyl, 2,2-dimethylbutyl, 2-ethylbutyl, 1,3-dimethylbutyl, 2-methylpentyl or 3-methylpentyl. The $C_{1-6}$ alkyl group may be, for example, and without limitation, interrupted by one or more heteroatoms which are independently nitrogen, sulfur or oxygen.

The $C_{2-6}$ alkenyl group of the $C_{2-6}$ alkenyl group which may be substituted, may be, for example, and without limitation, any straight or branched alkenyl, for example, vinyl, allyl, isopropenyl, 1-propene-2-yl, 1-butene-1-yl, 1-butene-2-yl, 1-butene-3-yl, 2-butene-1-yl or 2-butene-2-yl. The $C_{2-6}$ alkenyl group may be, for example, and without limitation, interrupted by one or more heteroatoms which are independently nitrogen, sulfur or oxygen.

The $C_{2-6}$ alkynyl group of the $C_{2-6}$ alkynyl group which may be substituted, may be, for example, and without limitation, any straight or branched alkynyl, for example, ethynyl, propynyl, butynyl, pentynyl or hexynyl. The $C_{2-6}$ alkynyl group may be, for example, and without limitation, interrupted by one or more heteroatoms which are independently nitrogen, sulfur or oxygen.

The $C_{3-8}$ cycloalkyl group of the $C_{3-8}$ cycloalkyl group which may be substituted, may be, for example, and without limitation, cyclopropanyl, cyclobutanyl, cyclopentanyl, cyclohexanyl or cycloheptanyl.

The $C_{3-8}$ cycloalkenyl group of the $C_{3-8}$ cycloalkenyl group which may be substituted, may be, for example, and without limitation, cyclopropenyl, cyclobutenyl, cyclopentenyl, cyclohexenyl or cycloheptenyl.

The $C_{6-14}$ aryl group of the aryl containing groups which may be substituted, may be, for example, and without limitation, phenyl, pentalenyl, indenyl, naphthyl, azulenyl, heptalenyl, benzocyclooctenyl or phenanthrenyl.

The $C_{6-14}$ aryl-$C_{1-6}$ alkyl group of the $C_{6-14}$ aryl-$C_{1-6}$ alkyl group which may be substituted, may be, for example, and without limitation, a $C_{1-6}$ alkyl group as defined anywhere above having a $C_{6-14}$ aryl group as defined anywhere above as a substituent.

The $C_{6-14}$ aryl-$C_{2-6}$ alkenyl group of the $C_{6-14}$ aryl-$C_{2-6}$ alkenyl group which may be substituted, may be, for example, and without limitation, a $C_{2-6}$ alkenyl group as defined anywhere above having a $C_{6-14}$ aryl group as defined anywhere above as a substituent.

The $C_{6-14}$ aryl-$C_{2-6}$ alkynyl group of the $C_{6-14}$ aryl-$C_{2-6}$ alkynyl group which may be substituted, may be, for example, and without limitation, a $C_{2-6}$ alkynyl group as defined anywhere above having a $C_{6-14}$ aryl group as defined anywhere above as a substituent.

The 4- to 10-membered non-aromatic heterocyclic group containing one or more heteroatoms which are independently nitrogen, sulfur or oxygen of the 4- to 10-membered non-aromatic heterocyclic group containing one or more heteroatoms which are independently nitrogen, sulfur or oxygen and which group may be substituted, may contain, for example, and without limitation, from 1 to 4 heteroatoms which are independently nitrogen, sulfur or oxygen. The 4- to 10-membered non-aromatic heterocyclic group containing one or more heteroatoms which are independently nitrogen, sulfur or oxygen may be, for example, and without limitation, pyrrolidinyl, pyrrolinyl, piperidinyl, piperazinyl, imidazolinyl, pyrazolidinyl, imidazolydinyl, morpholinyl, tetrahydropyranyl, azetidinyl, oxetanyl, oxathiolanyl, phthalimide or succinimide.

The 5- to 14-membered aromatic heterocyclic group containing one or more heteroatoms which are independently nitrogen, sulfur or oxygen of the 5- to 14-membered aromatic heterocyclic group containing one or more heteroatoms which are independently nitrogen, sulfur or oxygen and which group may be substituted, may contain, for example, and without limitation, from 1 to 4 heteroatoms which are independently nitrogen, sulfur or oxygen. The 5- to 14-membered aromatic heterocyclic group containing one or more heteroatoms which are independently nitrogen, sulfur or oxygen may be, for example, and without limitation, pyrrolyl, pyridinyl, pyridainyl, pyrimidinyl, pirazinyl, imidazolyl, thiazolyl or oxazolyl.

Each of the $C_{1-6}$ alkyl, $C_{2-6}$ alkenyl, $C_{2-6}$ alkynyl, $C_{3-8}$ cycloalkyl, $C_{3-8}$ cycloalkenyl, $C_{6-14}$ aryl, $C_{6-14}$ aryl-$C_{1-6}$ alkyl, $C_{6-14}$ aryl-$C_{2-6}$ alkenyl, $C_{6-14}$ aryl-$C_{2-6}$ alkynyl, 4- to 10-membered non-aromatic heterocylic and 5- to 14-membered aromatic heterocyclic groups may be substituted with one or more substituents which are the same or different. In an embodiment of the present invention, each of the above-mentioned groups may be substituted with, for example, and without limitation, one to three substituents.

The one or more substituents for each of the above-mentioned groups, which are the same or different, may be, for example, and without limitation, a halogen atom, a hydroxyl group, a thiol group, a nitro group, a nitrile group, a cyano group; a $C_{1-6}$ alkyl, $C_{2-6}$ alkenyl or $C_{2-6}$ alkynyl group which may be substituted; a $C_{3-8}$ cycloalkyl or $C_{3-8}$ cycloalkenyl group which may be, substituted; a $C_{6-14}$ aryl group which may be substituted; a $C_{6-14}$ aryl-$C_{1-6}$ alkyl, $C_{6-14}$ aryl-$C_{2-6}$ alkenyl or $C_{6-14}$ aryl-$C_{2-6}$ alkynyl group which may be substituted; a 4- to 10-membered non-aromatic heterocylic group containing 1 to 4 heteroatoms which are independently nitrogen, oxygen or sulfur and which group may be substituted, a 5- to 14-membered aromatic heterocylic group containing 1 to 4 heteroatoms which are independently nitrogen, oxygen or sulfur and which group may be substituted, a $C_{1-8}$ alkoxy group which may be substituted, $C_{3-8}$ cycloalkoxy group which may be substituted; a $C_{1-6}$ alkylthio, $C_{2-6}$ alkenylthio or $C_{2-6}$ alkynylthio group which may be substituted; a $C_{3-8}$ cycloalkylthio or $C_{3-8}$ cycloalkenylthio group which may be substituted; a $C_{6-14}$ aryloxy group which may be substituted, a 4- to 10-membered non-aromatic heterocycle-oxy group which may be substituted, a 5- to 14-membered aromatic heterocycle-oxy group which may be substituted, a $C_{6-14}$ arylthio group which may be substituted, a 4- to 10-membered non-aromatic heterocycle-thio group which may be substituted, a 5- to 14-membered aromatic heterocycle-thio group which may be substituted, an amino group which may be substituted, an azide group, a guanidino group, a carbamide group, a formyl group, a $C_{1-6}$ imidoyl group, a carbonyl group which is substituted, a carbonyl-oxy group which is substituted, a carboxy group, a carbamoyl group which may be substituted, a $C_{1-4}$ alkylenedioxy group, a sulfanyl group, a sulfinyl group which is substituted, a sulfonyl group which is substituted, a $C_{1-6}$ alkoxycarbonyl group, a $C_{1-6}$ alkylsulfonyl group, an oxo group or a $C_{1-6}$ alkoxyimino group.

In an embodiment of the present invention, $R_1$ is, for example, a $C_{1-6}$ alkyl group, a $C_{2-6}$ alkenyl group which may be substituted with $C_{1-6}$ alkoxycarbonyl, a $C_{3-8}$ cycloalkyl group, a $C_{6-14}$ aryl group which may be substituted with $C_{1-6}$ alkoxy, nitro or halogen, a $C_{6-14}$ aryl-$C_{1-6}$ alkyl group, a $C_{6-14}$ aryl-$C_{2-6}$ alkenyl group, a $C_{6-14}$ aryl-$C_{2-6}$ alkenyl group wherein the $C_{6-14}$ aryl may be substituted with one or more substituents which are independently $C_{1-6}$ alkoxy, nitro or trifluoromethylsulfonyl, or a 5- to 14-membered aromatic heterocyclic group containing 1 to 4 heteroatoms which are independently nitrogen, oxygen or sulfur and which group may be Substituted with $C_{1-6}$ alkyl.

B. Nitroso Compound

The nitroso compound which may be used in the present invention is not particularly limited.

In an embodiment of the present invention, the nitroso compound may be, for example, and without limitation, a compound represented by the formula (III):

(III)

wherein $R_2$ may be, for example, and without limitation, a $C_{1-6}$ alkyl group which may be substituted with one or more substituents which are the same or different, a $C_{2-6}$ alkenyl group which may be substituted with one or more substituents which are the same or different, a $C_{2-6}$ alkynyl group which may be substituted with one or more substituents which are the same or different, a $C_{3-8}$ cycloalkyl group which may be substituted with one or more substituents which are the same or different, a $C_{3-8}$ cycloalkenyl group which may be substituted with one or more substituents which are the same or different, a $C_{6-14}$ aryl group which may be substituted with one or more substituents which are the same or different, a $C_{6-14}$ aryl-$C_{1-6}$ alkyl group which may be substituted with one or more substituents which are the same or different, a $C_{6-19}$ aryl-$C_{2-6}$ alkenyl group which may be substituted with one or more substituents, which are the same or different, a $C_{6-14}$ aryl-$C_{2-6}$ alkynyl group which may be substituted with one or more substituents which are the same or different, a $C_{1-6}$ alkoxycarbonyl group which may be substituted with one or more substituents which are the same or different, a $C_{6-14}$ aryloxycarbonyl group which may be substituted with one or more substituents which are the same or different, an amino-$C_{1-6}$ alkyl group which may be substituted with one or more substituents which are the same or different, an amino-$C_{6-14}$ aryl group which may be substituted with one or more substituents which are the same or different, an acetyl group or an amido group.

Each of the $C_{1-6}$ alkyl, $C_{2-6}$ alkenyl, $C_{2-6}$ alkynyl, $C_{3-8}$ cycloalkyl, $C_{3-8}$ cycloalkenyl, $C_{6-14}$ aryl, $C_{6-14}$ aryl-$C_{1-6}$ alkyl, $C_{6-14}$ aryl-$C_{2-6}$ alkenyl, $C_{6-14}$ aryl-$C_{2-6}$ alkynyl, $C_{1-6}$ alkoxycarbonyl, $C_{6-14}$ aryloxycarbonyl, amino-$C_{1-6}$ alkyl and amino-$C_{6-14}$ aryl groups may be substituted with one or more substituents which are the same or different. In an embodiment of the present invention, each of the above-mentioned groups may be substituted with, for example, and without limitation, one to three substituents.

The one or more substituents for each of the above-mentioned groups, which are the same or different, may be, for example, and without limitation, the same substituents as defined anywhere above for the aldehyde.

In an exemplary embodiment of the present invention, $R_2$ may be, for example, and without limitation, a phenyl group which may be substituted with one or more substituents which are the same or different.

In an embodiment of the present invention, $R_2$ may be, for example, and without limitation, a phenyl group which may be substituted with one or more substituents, which are the same or different, and are a halogen atom, an amino group which may be substituted by $C_{1-6}$ alkyl, a $C_{1-6}$ alkyl group or a hydroxyl group.

C. Hydroxamic Acid

In an embodiment of the present invention, the hydroxamic acid may be, for example, and without limitation, a compound represented by the formula (I):

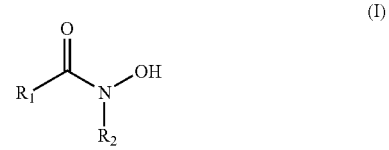

(I)

wherein $R_1$ and $R_2$ may be defined as anywhere above.

D. NHC Catalyst

The NHC catalyst that may be used in the present invention is not particularly limited.

In an embodiment of the present invention, the NHC catalyst may be derived from, for example, and without limitation, a triazolium salt or an imidazolium salt.

In an embodiment of the present invention, the NHC catalyst may be derived from, for example, and without limitation, a triazolium salt.

In an embodiment of the present invention, the NHC catalyst may be derived from, for example, and without limitation, a triazolium salt represented by the formula:

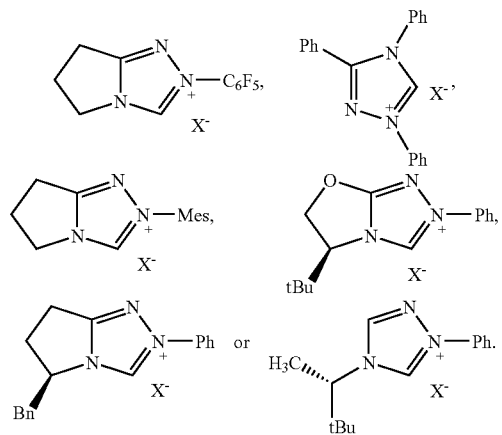

wherein $X^-$ may be, for example, and without limitation, NHC, $ClO_4^-$, $Br^-$ or $Cl^-$.

In an embodiment of the present invention, the NHC catalyst may be derived from, for example, a triazolium salt represented by the formula:

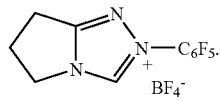

In an embodiment of the present invention, the NHC catalyst may be derived from, for example, a triazolium salt represented by the formula:

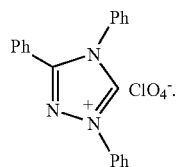

In an embodiment of the present invention, the NHC catalyst may be derived from, for example, and without limitation, a triazolium salt represented by the formula:

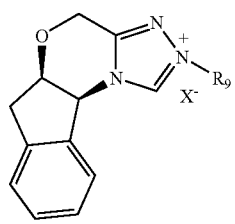

wherein $R_9$ may be, for example, and without limitation, phenyl (Ph) which may be substituted, i-propyl ($^i$Pr), mesityl (Mes) or 2,6-diisopropylphenyl (2,6-$^i$Pr-Ph); and $X^-$ may be, for example, and without limitation, $Br^-$, $BF_4^-$ or $Cr^-$.

In an embodiment of the present invention, the NHC catalyst may be derived from, for example, and without limitation, an imidazolium salt.

In an embodiment of the present invention, the NHC catalyst may be derived from, for example, and without limitation, an imidazolium salt represented by the formula:

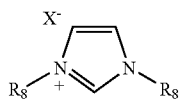

wherein $R_8$ may be, for example, and without limitation, phenyl (Ph), i-propyl ($^i$Pr), mesityl (Mes) or 2,6-diisopropylphenyl (2,6-$^i$Pr-Ph); and $X^-$ may be, for example, and without limitation, $Br^-$, $BF_4^-$ or $Cl^-$.

In an embodiment of the present invention, the NHC catalyst may be derived from, for example, an imidazolium salt represented by the formula:

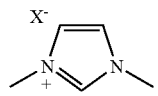

wherein $X^-$ may be, for example, and without limitation, $Br^-$, $BF_4^-$ or $Cl^-$.

E. Preparation of Hydroxamic Acid

In an embodiment of the present invention, and without limitation, there is provided a process for preparing a hydroxamic acid represented by the formula (I):

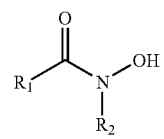

wherein $R_1$ and $R_2$ may be defined as anywhere above, which process comprises reacting an aldehyde represented by the formula (II):

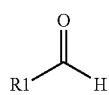

wherein $R_1$ may be defined as above, with a nitroso compound represented by the formula (III):

wherein $R_2$ may be defined as above, in the presence of a NHC catalyst.

An embodiment of the present invention may be represented by, for example, and without limitation, the following scheme:

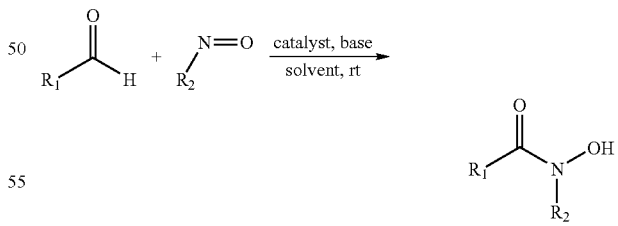

wherein $R_1$ and $R_2$ may be defined as anywhere above.

Without being bound by theory, it is believed that the polarization of the nitrogen-oxygen bond of the nitroso compound, resembling the polarization of the carbon-oxygen bond in a carbonyl group, provides the susceptibility of the nitroso group to additions of nucleophiles. By way of example, and without limitation, as represented in the following scheme, it is believed that the higher reactivity of the nitroso group to nucleophilic attack than its carbonyl group counterpart gives rise to the reaction of the intermediate ii with nitrosobenzene 2 forming a hydroxamic acid 3 instead of acyloin.

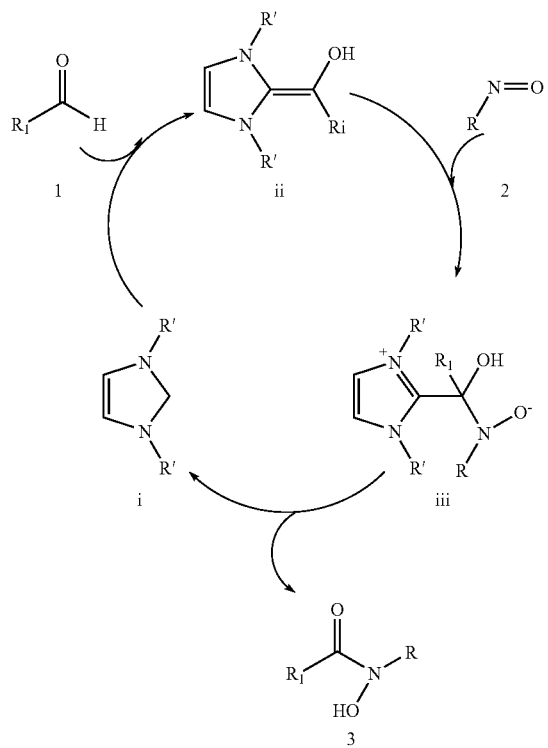

wherein $R_1$ is defined as anywhere above, R is phenyl and R' is a hydrocarbon group including those as defined for $R_1$ above.

The amounts of the aldehyde and nitroso compound which may be used in the present invention are not particularly limited. Suitable amounts of the aldehyde and nitroso compound would be understood to and can be determined by those of ordinary skill in the art. For example, and without limitation, those of ordinary skill in the art would understand that the aldehyde and nitroso compound may be used according to their stoichiometric ratio.

In an embodiment of the present invention, the aldehyde, nitroso compound and NHC catalyst may be, for example, and without limitation, reacted in the presence of a base. The base is not particularly limited and suitable bases would be understood to and can be determined by those of ordinary skill in the art. In an embodiment of the present invention, the base may be a non-nucleophilic base, for example, and without limitation, 1,8-diazabicyclo[5.4.0]undec-7-ene (DBU), potassium tert-butoxide (KO$^t$Bu), sodium bis(trimethylsilyl)amide, potassium bis(trimethylsilyl)amide, lithium tetramethylpiperidine or sodium tert-butoxide. In an embodiment of the present invention, the base may be, for example, 1,8-diazabicyclo[5.4.0]undec-7-ene or potassium tert-butoxide.

In an embodiment of the present invention, the reaction may be, for example, and without limitation, carried out in the presence of a suitable solvent. The solvent is not particularly limited and suitable solvents would be understood to and can be determined by those of ordinary skill in the art. In an embodiment of the present invention, the solvent may be, for example, and without limitation, an aprotic solvent. In an embodiment of the present invention, the solvent may be, for example, dichloromethane ($CH_2Cl_2$) or tetrahydrofuran (THF).

The amount of the NHC catalyst which may be used in the present invention is not particularly limited. Suitable amounts of the NHC catalyst would be understood to and can be determined by those of ordinary skill in the art. In an embodiment of the present invention, the amount of the NHC catalyst may be, for example, and without limitation, less than 20 mol %, for example, and without limitation, from 0.125 to 20 mol %, and including any specific value in this range, such as, for example, and without limitation, from 0.5 to 20 mol %.

The reaction time is not particularly limited and suitable reaction times would be understood to and can be determined by those of ordinary skill in the art. In an embodiment of the present invention, the reaction time may be, for example, and without limitation, less than 24 hours, for example, and without limitation, from 2 minutes to 24 hours, and including any specific time in this range, such as, for example, and without limitation, from 1 to 12 hours.

The reaction temperature is not particularly limited and suitable reaction temperatures would be understood to and can be determined by those of ordinary skill in the art. In an embodiment of the present invention, the reaction temperature may be, for example, and without limitation, room temperature.

In an embodiment of the present invention, the hydroxamic acid may be isolated and/or purified. Suitable isolation and/or purification methods would be understood to and can be determined by those of ordinary skill in the art. For example, and without limitation, those of ordinary skill in the art would understand that the hydroxamic acid may be isolated and/or purified by chromatographic methods or crystallization.

F. Process for Preparing Chiral Hydroxamic Acid

The above process for preparing the hydroxamic acid may be modified as described below in order to prepare a chiral hydroxamic acid using an achiral NHC catalyst.

In an embodiment of the present invention, a α-branched aldehyde may be reacted with a nitroso compound in the presence of an achiral NHC catalyst to prepare a chiral hydroxamic acid.

In an embodiment of the present invention, a α-branched aldehyde which may have one enantiomer in excess of the other (i.e., in enantiomeric excess or "ee") or which may be enantiomerically pure may be reacted with a nitroso compound in the presence of an achiral NHC catalyst to prepare a chiral hydroxamic acid which may be in enantiomeric excess or which may be enantiomerically pure.

In an embodiment of the present invention, an enantiomerically pure α-branched aldehyde may be reacted with a nitroso compound in the presence of an achiral NHC catalyst to prepare an enantiomerically pure chiral hydroxamic acid.

The achiral NHC catalyst is not particularly limited and suitable achiral NHC catalysts would be understood to and can be determined by those of ordinary skill in the art.

In an embodiment of the present invention, the achiral NHC catalyst may be derived from, for example, and without limitation, an achiral triazolium salt.

In an embodiment of the present invention, the achiral triazolium salt may be represented by, for example, the formula:

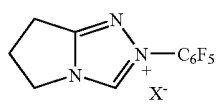

wherein X⁻ may be, for example, and without limitation, $BF_4^-$, $ClO_4^-$, $Br^-$ or $Cl^-$.

The skilled person will appreciate that the amount of the α-branched aldehyde, the amount of the nitroso compound, the base, the solvent, the amount of the NHC catalyst, the reaction time, the reaction temperature, the isolation methods and the purification methods described above may also be used for preparing the chiral hydroxamic acid as described herein.

An embodiment of the present invention for preparing the chiral hydroxamic acid may be represented by, for example, and without limitation, the following scheme:

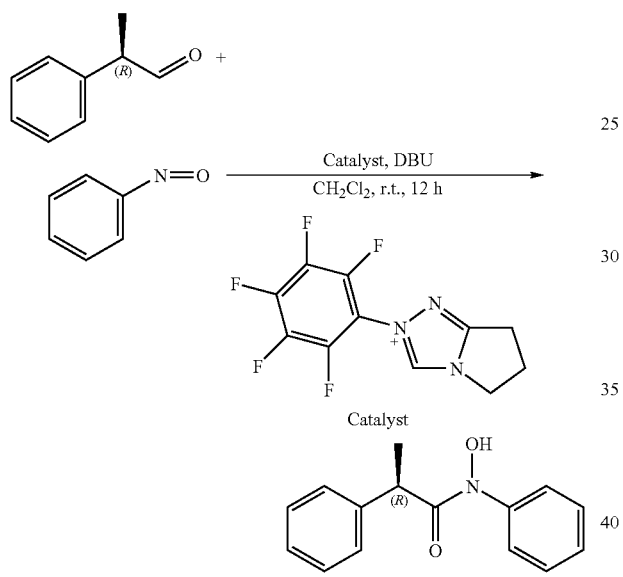

The above process for preparing the hydroxamic acid may also be modified as described below in order to prepare a chiral hydroxamic acid using a chiral NHC catalyst.

In an embodiment of the present invention, a α-branched aldehyde may be reacted with a nitroso compound in the presence of a chiral NHC catalyst to prepare a chiral hydroxamic acid.

In an embodiment of the present invention, a α-branched aldehyde may be reacted with a nitroso compound in the presence of a chiral NHC catalyst to prepare a chiral hydroxamic acid in enantiomeric excess.

In an embodiment of the present invention, a α-branched aldehyde racemate may be reacted with a nitroso compound in the presence of a chiral NHC catalyst to prepare a chiral hydroxamic acid in enantiomeric excess.

In an embodiment of the present invention, a α-branched aldehyde racemate may be reacted with a nitroso compound in the presence of a chiral NHC catalyst to prepare a chiral hydroxamic acid in enantiomeric excess, wherein a stoichiometric excess of the α-branched aldehyde racemate is reacted.

In an embodiment of the present invention, a α-branched aldehyde racemate may be reacted with a nitroso compound in the presence of a chiral NHC catalyst to prepare a chiral hydroxamic acid in enantiomeric excess, wherein a stoichiometric excess of the α-branched aldehyde racemate is reacted and the reaction is stopped at less than 100% conversion of the aldehyde.

In an embodiment of the present invention, a α-branched aldehyde racemate may be reacted with a nitroso compound in the presence of a chiral NHC catalyst to prepare a chiral hydroxamic acid in enantiomeric excess, wherein a stoichiometric excess of the α-branched aldehyde racemate is reacted and the reaction is stopped at about 50% conversion of the aldehyde.

The chiral NHC catalyst is not particularly limited and suitable chiral NHC catalysts would be understood to and can be determined by those of ordinary skill in the art.

In an embodiment of the present invention, the chiral NHC catalyst may be derived from, for example, and without limitation, a chiral triazolium salt.

In an embodiment of the present invention, the chiral triazolium salt may be represented by, for example, the formula:

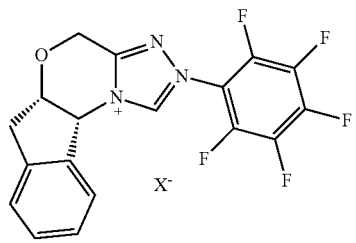

wherein X⁻ may be, for example, and without limitation, $BF_4^-$, $ClO_4^-$, $Br^-$ or $Cl^-$.

In an embodiment of the present invention, the chiral triazolium salt may be represented by, for example, the formula:

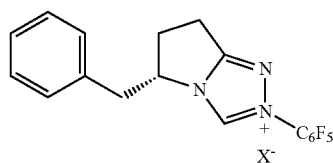

wherein X⁻ may be, for example, and without limitation, $BF_4^-$, $ClO_4^-$, $Br^-$ or $Cl^-$.

In an embodiment of the present invention, the chiral triazolium salt may be represented by, for example, the formula:

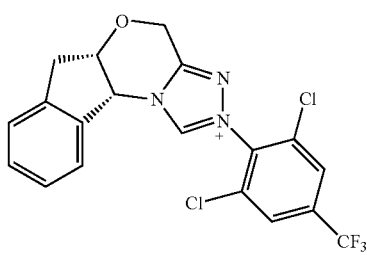

wherein X⁻ may be, for example, and without limitation, $BF_4^-$, $ClO_4^-$, $Br^-$ or $Cl^-$.

In an embodiment of the present invention using a chiral catalyst, a stoichiometric excess of the α-branched aldehyde may be used. Suitable amounts of the aldehyde would be understood to and can be determined by those of ordinary skill in the art. For example, and without limitation, those of ordinary skill in the art would understand that a ratio of the α-branched aldehyde to the nitroso compound of 2:1 may be used.

In an embodiment of the present invention using a chiral catalyst, for example, and without limitation, the reaction may proceed with less than 100% conversion of the α-branched aldehyde. Suitable amounts of conversion of the α-branched aldehyde would be understood to and can be determined by those of ordinary skill in the art. For example, and without limitation, those of ordinary skill in the art would understand that the reaction may proceed with about 50% conversion of the α-branched aldehyde.

The skilled person will appreciate that the base, the solvent, the amount of the NHC catalyst, the reaction time, the reaction temperature, the isolation methods and the purification methods described above may also be used for preparing the chiral hydroxamic acid as described herein.

An embodiment of the present invention for preparing the chiral hydroxamic acid by kinetically resolving the α-branched aldehyde may be represented by, for example, and without limitation, the following scheme:

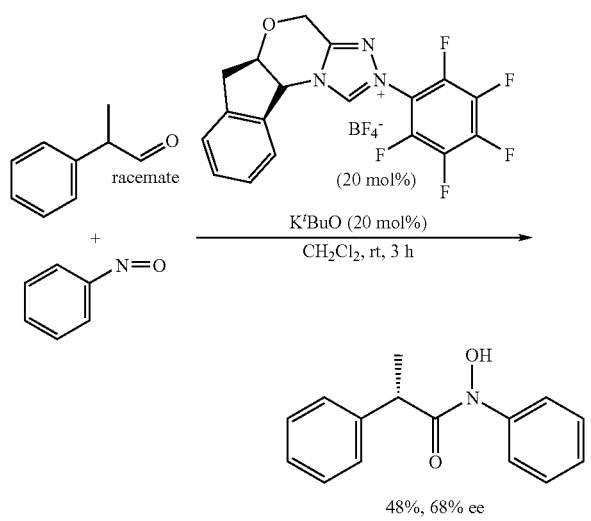

In an embodiment of the present invention using either an achiral or chiral catalyst, the α-branched aldehyde may be, for example, and without limitation, a compound represented by the formula (V):

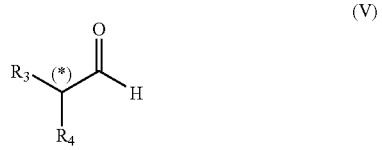

wherein:
(*) refers to a chiral center; and
$R_3$ and $R_4$, which are different, may be for example, and
  Without limitation, a halogen atom, a hydroxyl group, a thiol group, a nitro group, a nitrile group, a cyano group; a $C_{1-6}$ alkyl, $C_{2-6}$ alkenyl or $C_{2-6}$ alkynyl group which may be substituted; a $C_{3-8}$ cycloalkyl or $C_{3-8}$ cycloalkenyl group which may be substituted; a $C_{6-14}$ aryl group which may be substituted, a $C_{6-14}$ aryl-$C_{1-6}$ alkyl group which may be substituted, a $C_{6-14}$ aryl-$C_{2-6}$ alkenyl group which may be substituted, a $C_{6-14}$ aryl-$C_{2-6}$ alkynyl group which may be substituted, a 4- to 10-membered non-aromatic heterocylic group containing 1 to 4 heteroatoms which are independently nitrogen, oxygen or sulfur and which group may be substituted, a 5- to 14-membered aromatic heterocylic group containing 1 to 4 heteroatoms which are independently nitrogen, oxygen or sulfur and which group may be substituted, a $C_{1-6}$ alkoxy group which may be substituted, a $C_{3-8}$ cycloalkoxy group which may be substituted; a $C_{1-6}$ alkylthio, $C_{2-6}$ alkenylthio or $C_{2-6}$ alkynylthio group which may be substituted; a $C_{3-8}$ cycloalkylthio or $C_{3-8}$ cycloalkenylthio group which may be substituted; a $C_{6-14}$ aryloxy group which may be substituted, a 4- to 10-membered non-aromatic heterocycle-oxy group which may be substituted, a 5- to 14-membered aromatic heterocycle-oxy group which may be substituted, a $C_{6-14}$ arylthio group which may be substituted, a 4- to 10-membered non-aromatic heterocycle-thio group which may be substituted, a 5- to 14-membered aromatic heterocycle-thio group which may be substituted, an amino group which may be substituted, an azide group, a guanidino group, a carbamide group, a formyl group, a $C_{1-6}$ imidoyl group, a carbonyl group which is substituted, a carbonyl-oxy group which is substituted, a carboxy group, a carbamoyl group which may be substituted, a $C_{1-4}$ alkylenedioxy group, a sulfanyl group, a sulfinyl group which is substituted, a sulfonyl group which is substituted, a $C_{1-6}$ alkoxycarbonyl group, a $C_{1-6}$ alkylsulfonyl group, an oxo group or a $C_{1-6}$ alkoxyimino group.

In an embodiment of the present invention, $R_3$, for example, is a $C_{1-6}$ alkyl group.

In an embodiment of the present invention, $R_4$, for example, is a phenyl group.

In an embodiment of the present invention using either an achiral or chiral catalyst, the chiral hydroxamic acid may be, for example, and without limitation, a compound represented by the formula (IV):

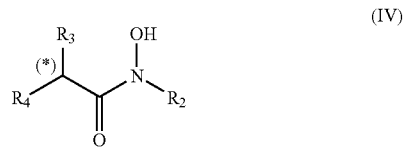

wherein (*), $R_2$, $R_3$ and $R_4$ are as defined anywhere above.

Non-limiting examples of one process of the present invention are described in more detail herein.

G. Examples

All reactions were performed in oven-dried (140° C.) or flame-dried glassware under an inert atmosphere of dry nitrogen or argon. All reaction solvents were anhydrous, and were purchased from Aldrich or Fluka.

In general, reactions were monitored by thin layer chromatography using 0.25 mm E. Merck silica gel coated glass plates (60F-254) with UV light to visualize the course of reaction. Flash column chromatography was performed using CombiFlash™ (ISCO, Inc.).

Chemical yields refer to pure isolated substances.

Gas chromatography-mass spectrometry (GC-MS) was conducted using Shimadzu™ GC-2010 coupled with GCMS-QP2010.

$^1$H and $^{13}$C. nuclear magnetic resonance (NMR) spectra were obtained using a Brucker™ AV-400 (400 MHz) spectrometer. Chemical shifts were reported in ppm from tetramethylsilane with the solvent resonance as the internal standard. Data were reported in the following order: chemical shift in ppm (δ) (multiplicity were indicated by br (broadened), s (singlet), d (doublet), t (triplet), q (quartet), m (multiplet), $m_c$ (centered multiplet)); coupling constants (J, Hz); integration; assignment.

Studies using different NHC catalysts were conducted by adding base ($5 \times 10^{-3}$ to 0.02 mmol) under argon to a solution of benzaldehyde (10.6 mg, 0.1 mmol), nitroso compound (10.7 mg, 0.1 mmol) and the catalyst ($5 \times 10^{-3}$ to 0.02 mmol) in solvent (0.5 ml). The reaction mixture was stirred at room temperature for 10 min. The yields were determined by GC.

N-hydroxy-N-phenylbenzamide

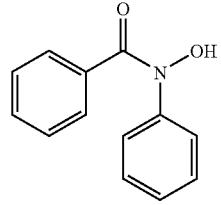

DBU (3.8 mg, 0.025 mmol) was added under argon to a solution of benzaldehyde (106 mg, 1 mmol), nitrosobenzene (107 mg, 1 mmol) and catalyst (1.82 mg, 0.005 mmol) in dichloromethane (5 mL). The reaction mixture was stirred at room temperature for 10 min. The solvent was removed under vacuum, and the residue was purified by flash silica gel column chromatography using hexane and ethyl acetate as the eluents.

$^1$H (400 MHz, CDCl$_3$): δ=9.05 (br s, 1H, OH), 7.45-7.36 (m, 3H, Ar—H), 7.33-7.25 (m, 5H, Ar—H), 7.22-7.19 (m, 2H, Ar—H). $^{13}$C (100 MHz, CDCl$_3$): δ=164.9 ($C_q$, CO), 139.1 ($C_q$), 131.8 ($C_q$), 131.1, 129.2, 128.9, 128.3, 128.2, 126.0. MS (ESI): m/z 197 (M$^+$-O), 105, 77.

N-hydroxy-4-methoxy-N-phenylbenzamide

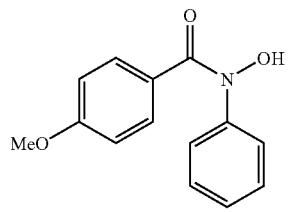

DBU (7.61 mg, 0.05 mmol) was added under argon to a solution of 4-methoxybenzaldehyde (136 mg, 1 mmol), nitrosobenzene (107 mg, 1 mmol) and catalyst (18.15 mg, 0.05 mmol) in dichloromethane (5 mL). The reaction mixture was stirred at room temperature for 10 min. The solvent was removed under vacuum, and the residue was purified by flash silica gel column chromatography using hexane and ethyl acetate as the eluents.

$^1$H (400 MHz, CDCl$_3$): δ=9.07 (br s, 1H, OH), 7.40 (AB, d, $J_{AB}$=8.9 Hz, 2H, Ar—H), 7.35-7.28 (m, 3H, Ar—H), 7.24-7.22 (m, 2H, Ar—H), 6.76 (AB, d, $J_{AB}$=8.9 Hz, 2H, Ar—H), 3.79 (s, 3H, CH$_3$). $^{13}$C (100 MHz, CDCl$_3$): δ=165.1 ($C_q$, CO), 161.7 ($C_q$), 140.4 ($C_q$), 131.0, 129.1, 127.9, 125.9, 124.3 ($C_q$), 113.4, 55.3. MS (ESI): m/z 227 (M$^+$-O), 135, 107, 92, 77.

N-hydroxy-4-nitro-N-phenylbenzamide

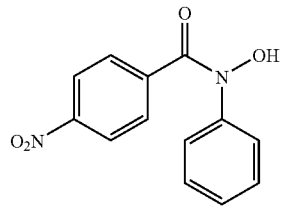

DBU (3.8 mg, 0.025 mmol) was added under argon to a solution of 4-nitrobenzaldehyde (151 mg, 1 mmol), nitroso benzene (107 mg, 1 mmol) and catalyst (1.82 mg, 0.005 mmol) in dichloromethane (5 mL). The reaction mixture was stirred at room temperature for 10 min. The solvent was removed under vacuum, and the residue was purified by flash silica gel column chromatography using hexane and ethyl acetate as the eluents.

Scale up: DBU (3.8 mg, 0.025 mmol) was added under argon to a solution of 4-nitrobenzaldehyde (3 g, 20 mmol), nitrosobenzene (2.14 g, 20 mmol) and catalyst (9 mg, 0.025 mmol) in dichloromethane (100 mL). The reaction mixture was stirred at room temperature for 2 min. The product precipitated as a yellow solid. The solvent was removed under vacuum, and the solid was washed with hexane and ether to yield a pure product (5 g).

$^1$H (400 MHz, CDCl$_3$): δ=8.93 (br s, 1H, OH), 8.13 (AB, d, $J_{AB}$=9.1 Hz, 2H, Ar—H), 7.60 (AB, d, $J_{AB}$=9.1 Hz, 2H, Ar—H), 7.36-7.34 (m, 3H, Ar—H), 7.24-7.22 (m, 2H, Ar—H). $^{13}$C (100 MHz, CDCl$_3$): δ=162.7 ($C_q$, CO), 148.9 ($C_q$), 138.3, 138.0, 130.0, 129.5, 129.1 ($C_q$), 126.2, 123.4. MS (ESI): m/z 242 (M$^+$-O), 150, 134, 120, 104, 92, 76.

4-Bromo-N-hydroxy-N-phenylbenzamide

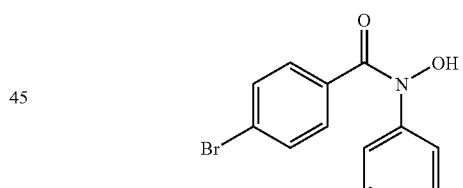

DBU (3.8 mg, 0.025 mmol) was added under argon to a solution of 4-bromobenzaldehyde (185 mg, 1 mmol), nitrosobenzene (107 mg, 1 mmol) and catalyst (1.82 mg, 0.005 mmol) in dichloromethane (5 mL). The reaction mixture was stirred at room temperature for 10 min. The solvent was removed under vacuum, and the residue was purified by flash silica gel column chromatography using hexane and ethyl acetate as the eluents.

$^1$H (400 MHz, CDCl$_3$): δ=9.00 (br s, 1H, OH), 7.41 (AB, d, $J_{AB}$=8.7 Hz, 2H, Ar—H), 7.36-7.31 (m, 3H, Ar—H), 7.29 (AB, d, $J_{AB}$=8.7 Hz, 2H, Ar—H), 7.22-7.20 (m, 2H, Ar—H). $^{13}$C (100 MHz, CDCl$_3$): δ=164.6 ($C_q$, CO), 139.3 ($C_q$), 131.5, 130.7 ($C_q$), 130.5, 129.3, 128.6, 126.1, 125.8 ($C_q$). MS (ESI): m/z 275 (M$^+$-O), 183, 155, 104, 76.

N-hydroxy-1-methyl-N-phenyl-1H-imidazole-2-carboxamide

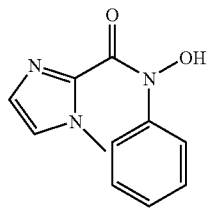

DBU (3.8 mg, 0.025 mmol) was added under argon to a solution of 1-methyl-1H-imidazole-2-carbaldehyde (110 mg, 1 mmol), nitrosobenzene (107 mg, 1 mmol) and catalyst (1.82 mg, 0.005 mmol) in dichloromethane (5 mL). The reaction mixture was stirred at room temperature for 10 min. The solvent was removed under vacuum, and the residue was purified by flash silica gel column chromatography using hexane and ethyl acetate as the eluents.

$^1$H (400 MHz, CDCl$_3$): δ=13.64 (br s, 1H, OH), 7.81 (d, J=7.4 Hz, 2H, Ar—H), 7.42 (td, J=2.0, 7.4 Hz, 2H, Ar—H), 7.24 (td, J=1.2, 7.4 Hz, 1H, Ar—H), 7.11 (d, J=1.1 Hz, 2H, HC=), 7.04 (d, J=1.1 Hz, 1H, HC=), 4.12 (s, 3H, CH$_3$). $^{13}$C (100 MHz, CDCl$_3$): δ=153.7 ($C_q$, CO), 139.7 ($C_q$), 139.0 ($C_q$), 128.5, 126.2, 125.8, 125.1, 122.3, 36.2. MS (ESI): m/z 201 (M$^+$-O), 184, 172, 159, 109, 82.

N-hydroxy-N,2-diphenylpropanamide

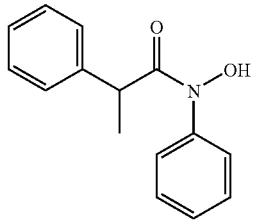

DBU (30 mg, 0.2 mmol) was added under argon to a solution of 2-phenylpropanal (134 mg, 1 mmol), nitrosobenzene (107 mg, 1 mmol) and catalyst (72.8 mg, 0.2 mmol) in dichloromethane (5 mL). The reaction mixture was stirred at room temperature for 10 min. The solvent was removed under vacuum, and the residue was purified by flash silica gel column chromatography using hexane and ethyl acetate as the eluents.

$^1$H (400 MHz, CDCl$_3$): δ=8.91 (br s, 1H, OH), 7.42-7.39 (m, 3H, Ar—H), 7.28-7.21 (m, 5H, Ar—H), 7.15-7.10 (m, 2H, Ar—H), 3.72 (br s, 1H, CH), 1.50 (br s, J=7.0 Hz, 3H, CH$_3$). $^{13}$C (100 MHz, CDCl$_3$): δ=169.5 ($C_q$, CO), 140.7 ($C_q$), 138.1 ($C_q$), 129.5, 129.4, 128.7, 127.7, 127.4, 127.1, 41.9, 19.8. MS (ESI): m/z 225 (M$^+$-O), 132, 120, 105, 93, 77.

N-Hydroxy-N,3-diphenylpropanamide

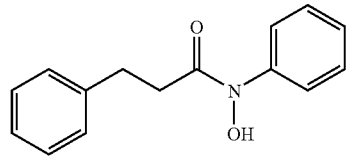

DBU (15 mg, 0.1 mmol) was added under argon to a solution of 3-phenylpropanal (134 mg, 1 mmol), nitrosobenzene (107 mg, 1 mmol) and catalyst (36.4 mg, 0.1 mmol) in dichloromethane (5 mL). The reaction mixture was stirred at room temperature for 10 min. The solvent was removed under vacuum, and the residue was purified by flash silica gel column chromatography using hexane and ethyl acetate as the eluents.

$^1$H (400 MHz, CDCl$_3$): δ=9.34 (br s, 1H, OH), 7.40-7.10 (m, 10H, Ar—H), 2.97 (t, J=7.4 Hz, 2H, CH$_2$), 2.57 (br s, 2H, CH$_2$). $^{13}$C (100 MHz, CDCl$_3$): δ=167.7, 140.3, 138.2, 129.3, 128.7, 128.6, 128.4, 126.9, 126:4, 34.2, 31.4. MS (ESI): m/z 225 (M$^+$-O), 105, 93.

N-hydroxy-N-phenylcyclohexanecarboxamide

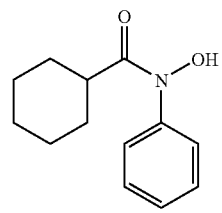

DBU (15 mg, 0.1 mmol) was added under argon to a solution of cyclohexanal (112 mg, 1 mmol), nitrosobenzene (107 mg, 1 mmol) and catalyst (36.4 mg, 0.1 mmol) in dichloromethane (5 mL). The reaction mixture was stirred at room temperature for 10 min. The solvent was removed under vacuum, and the residue was purified by flash silica gel column chromatography using hexane and ethyl acetate as the eluents.

$^1$H (400 MHz, CDCl$_3$): δ=9.15 (br s, 1H, OH), 7.48-7.30 (m, 5H, Ar—H), 2.33 (br s, 1H, CH), 1.77-1.67 (m, 4H, CH$_2$), 1.65-1.55 (m, 3H, CH$_2$), 1.27-1.15 (m, 1H, CH$_2$), 1.14-1.01 (m, 2H, CH$_2$). $^{13}$C (100 MHz, CDCl$_3$): δ=171.5 ($C_q$, CO), 138.2 ($C_q$), 129.4, 129.2, 126.7, 40.2, 29.1, 25.6, 25.5, 25.4. MS (ESI): m/z 203 (M$^+$-O), 148, 93, 83.

N-hydroxy-N-phenylcyclopropanecarboxamide

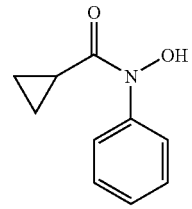

DBU (15 mg, 0.1 mmol) was added under argon to a solution of cyclopropanal (70 mg, 1 mmol), nitrosobenzene (107 mg, 1 mmol) and catalyst (36.4 mg, 0.1 mmol) in dichloromethane (5 mL). The reaction mixture was stirred at room temperature for 10 min. The solvent was removed under vacuum, and the residue was purified by flash silica gel column chromatography using hexane and ethyl acetate as the eluents.

$^1$H (400 MHz, CDCl$_3$): δ=8.81 (br s, 1H, OH), 7.50-7.43 (m, 4H, Ar—H), 7.40-7.36 (m, 1H, Ar—H), 1.68 (s, 1H, CH), 1.17-1.13 (dddd, J=3.0, 3.8, 4.7, 7.8 Hz, 2H, CH$_2$), 0.85-0.80 (dddd, J=3.0, 3.8, 4.1, 7.8 Hz, 2H, CH$_2$). $^{13}$C (100 MHz, CDCl$_3$): δ=170.6 ($C_q$, CO), 139.7 ($C_q$), 129.1, 128.3, 126.2, 11.7, 8.5. MS (ESI): m/z 161 (M$^+$-O), 106, 93, 77.

N-hydroxy-N-phenylpentanamide

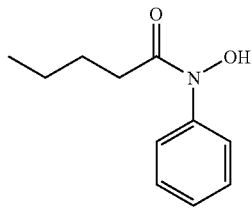

DBU (15 mg, 0.1 mmol) was added under argon to a solution of pentanal (86 mg, 1 mmol), nitrosobenzene (107 mg, 1 mmol) and catalyst (36.4 mg, 0.1 mmol) in dichloromethane (5 mL). The reaction mixture was stirred at room temperature for 30 min. The solvent was removed under vacuum, and the residue was purified by flash silica gel column chromatography using hexane and ethyl acetate as the eluents.

$^1$H (400 MHz, CDCl$_3$): δ=9.25 (br s, 1H, OH), 7.47-7.43 (m, 2H, Ar—H), 7.41-7.37 (m, 3H, Ar—H), 2.31 (br t, J=7.4 Hz, 2H, CH$_2$), 1.64 (pentet, J=7.4 Hz, 2H, CH$_2$), 1.29 (sextet, J=7.4 Hz, 2H, CH$_2$), 0.85 (t, J=7.4 Hz, 3H, CH$_3$). $^{13}$C (100 MHz, CDCl$_3$): δ=169.3 (C$_q$, CO), 138.8 (C$_q$), 129.2, 126.8, 121.4, 32.3, 27.4, 22.3, 13.8. MS (ESI): m/z 177 (M$^+$-O), 135, 93.

(E)-N-hydroxy-N-phenylcinnamamide

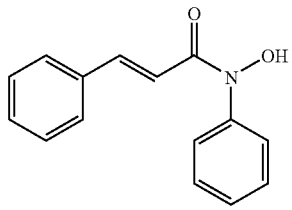

DBU (15 mg, 0.1 mmol) was added under argon to a solution of (E)-cinnamaldehyde (132 mg, 1 mmol), nitrosobenzene (107 mg, 1 mmol) and catalyst (36.4 mg, 0.1 mmol) in dichloromethane (5 mL). The reaction mixture was stirred at room temperature for 10 min. The solvent was removed under vacuum, and the residue was purified by flash silica gel column chromatography using hexane and ethyl acetate as the eluents.

$^1$H (400 MHz, CDCl$_3$): δ=9.3 (br s, 1H, OH), 7.78 (d, J=15.6 Hz, 1H, HC=), 7.51-7.39 (m, 7H, Ar—H), 7.35-7.33 (m, 3H, Ar—H), 6.55 (d, J=15.6 Hz, 1H, HC=). $^{13}$C (100 MHz, CDCl$_3$): δ=161.8 (C$_q$, CO), 143.1 (C$_q$), 137.8, 134.6, 130.1, 129.3, 129.0, 128.8, 128.0, 126.2, 115.1. MS (ESI): m/z 223 (M$^+$-O), 131, 103, 93, 77.

(E)-N-hydroxy-2-methyl-N,3-diphenylacrylamide

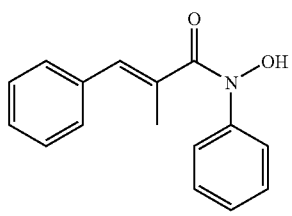

DBU (15 mg, 0.1 mmol) was added under argon to a solution of (E)-2-methyl-3-phenylacrylaldehyde (146 mg, 1 mmol), nitrosobenzene (107 mg, 1 mmol) and catalyst (36.4 mg, 0.1 mmol) in dichloromethane (5 mL). The reaction mixture was stirred at room temperature for 10 min. The solvent was removed under vacuum, and the residue was purified by flash silica gel column chromatography using hexane and ethyl acetate as the eluents.

$^1$H (400 MHz, CDCl$_3$): δ=9.04 (br s, 2H, OH), 7.43-7.38 (m, 4H, Ar—H), 7.37-7.30 (m, 3H, Ar—H), 7.28-7.24 (m, 1H, Ar—H), 7.16-7.14 (m, 2H, Ar—H), 6.84 (s, 1H, HC=), 1.96 (d, J=1.5 Hz, 3H, CH$_3$). $^{13}$C (100 MHz, CDCl$_3$): δ=167.8 (C$_q$, CO), 140.6 (C$_q$), 137.7, 136.8, 130.9 (C$_q$), 130.6, 130.4, 129.7, 129.4, 126.8, 15.8. MS (ESI): m/z 237 (M$^+$-O), 145, 117, 91.

(E)-N-hydroxy-3-(4-methoxyphenyl)-N-phenylacrylamide

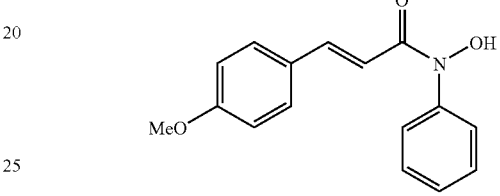

DBU (7.5 mg, 0.05 mmol) was added under argon to a solution of (E)-4-methoxycinnamaldehyde (162 mg, 1 mmol), nitrosobenzene (107 mg, 1 mmol) and catalyst (18.2 mg, 0.05 mmol) in dichloromethane (5 mL). The reaction mixture was stirred at room temperature for 10 min. The solvent was removed under vacuum, and the residue was purified by flash silica gel column chromatography using hexane and ethyl acetate as the eluents.

$^1$H (400 MHz, CDCl$_3$): δ=9.18 (br s, 1H, OH), 7.73 (d, J=15.6 Hz, 1H, HC=), 7.50-7.40 (m, 5H, Ar—H), 7.36 (AB, d, J$_{AB}$=8.8 Hz, 2H, Ar—H), 6.85 (AB, d, J$_{AB}$=8.8 Hz, 2H, Ar—H), 6.43 (d, J=15.6 Hz, 1H, HC=), 3.81 (s, 3H, CH$_3$). $^{13}$C (100 MHz, CDCl$_3$): δ=161.2 (C$_q$, CO), 142.7 (C$_g$), 137.8 (C$_q$), 129.7, 129.1, 128.9, 128.6, 127.4 (C$_q$), 126.1, 114.2, 112.5, 55.4. MS (ESI): m/z 253 (M$^+$-O), 161, 133, 118.

(E)-N-hydroxy-3-(4-nitrophenyl)-N-phenylacrylamide

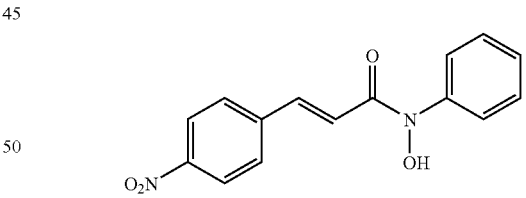

DBU (7.5 mg, 0.05 mmol) was added under argon to a solution of (E)-4-nitrocinnamaldehyde (177 mg, 1 mmol), nitrosobenzene (107 mg, 1 mmol) and catalyst (18.2 mg, 0.05 mmol) in dichloromethane (5 mL). The reaction mixture was stirred at room temperature for 10 min. The solvent was removed under vacuum, and the residue was purified by flash silica gel column chromatography using hexane and ethyl acetate as the eluents.

$^1$H (400 MHz, CDCl$_3$): δ=9.64 (br s, 1H, OH), 8.13 (d, J=15.3 Hz, 1H, =CH), 7.98 (d, J=8.1 Hz, 1H, Ar—H), 7.57-7.39 (m, 8H, Ar—H), 6.42 (br s, 1H, =CH). $^{13}$C (100 MHz, CDCl$_3$): δ=160.6 (C$_q$, CO), 148.2, 138.3, 133.4, 130.9, 130.0, 129.5, 129.2, 126.6, 124.8, 120.7. MS (ESI): 268 (M$^+$-O), 176, 148.

4-[(E)-2-(N-hydroxy-N-phenylcarbamoyl)vinyl]-2-methoxyphenyl trifluoromethanesulfonate

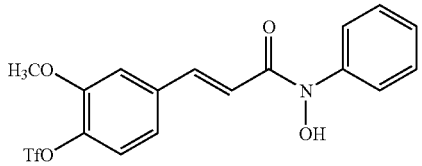

DBU (15 mg, 0.1 mmol) was added under argon to a solution of (E)-3-methoxy-4-trifluoromethyl sulfonyloxycinnamaldehyde (310 mg, 1 mmol), nitrosobenzene (107 mg, 1 mmol) and catalyst (36.4 mg, 0.1 mmol) in dichloromethane (5 mL). The reaction mixture was stirred at room temperature for 10 min. The solvent was removed under vacuum, and the residue was purified by flash silica gel column chromatography using hexane and ethyl acetate as the eluents.

$^1$H (400 MHz, CDCl$_3$): δ=9.24 (br s, 1H, OH), 7.72 (d, J=15.5 Hz, 1H, =CH), 7.53-7.44 (m, 5H, Ar—H), 7.18 (d, J=8.6 Hz, 1H, Ar—H), 7.03 (d, J=8.6 Hz, 1H, Ar—H), 7.02 (s, 1H, Ar—H), 6.53 (br s, 1H, =CH), 3.91 (s, 3H, OMe). $^{13}$C (100 MHz, CDCl$_3$): δ=160.7 (C$_g$, CO), 151.6, 141.2, 139.4, 135.9, 129.2, 129.4, 126.3, 122.8, 120.3, 120.1, 117.1, 113.9, 112.5, 56.2. HRMS (ESI), calcd for C$_{17}$H$_{14}$O$_5$NF$_3$S (M$^+$-O) 401.0545, found 401.0549

(E)-Ethyl 3-(N-hydroxy-N-phenylcarbamoyl)acrylate

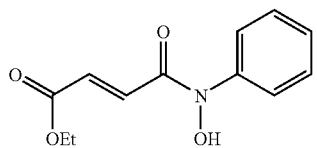

DBU (7.5 mg, 0.05 mmol) was added under argon to a solution of (E)-ethyl 3-formylacrylate (128 mg, 1 mmol), nitrosobenzene (107 mg, 1 mmol) and catalyst (18.2 mg, 0.05 mmol) in dichloromethane (5 mL). The reaction mixture was stirred at room temperature for 10 min. The solvent was removed under vacuum, and the residue was purified by flash silica gel column chromatography using hexane and ethyl acetate as the eluents.

$^1$H (400 MHz, CDCl$_2$): S=9.68 (br s, 1H, OH), 7.44-7.34 (br m, 5H, Ar—H), 6.97-6.90 (br m, 2H, Ar—H), 4.20 (q, J=7.2 Hz, 2H, CH$_2$), 1.27 (t, J=7.2 Hz, 3H, CH$_2$). $^{13}$C (100 MHz, CDCl$_3$): δ=165.2, 159.3, 137.1, 131.9, 131.0, 129.6, 128.9, 126.5, 61.3, 14.1. HRMS (ESI), calcd for C$_{12}$H$_{13}$O$_3$N (M$^+$-O) 219.0895, found 219.0894.

N-hydroxy-N-phenylacrylamide

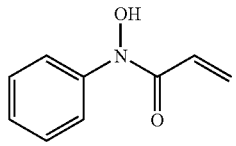

DBU (15 mg, 0.1 mmol) was added under argon to a solution of acrolein (56 mg, 1 mmol), nitrosobenzene (107 mg, 1 mmol) and catalyst (36.4 mg, 0.1 mmol) in dichloromethane (5 mL). The reaction mixture was stirred at room temperature for 10 min. The solvent was removed under vacuum, and the residue was purified by flash silica gel column chromatography using hexane and ethyl acetate as the eluents.

$^1$H (400 MHz, CDCl$_2$): S=9.15 (br s, 1H, OH), 7.49-7.40 (m, 5H, Ar—H), 6.50 (dd, J=1.6, 16.9 Hz, 1H, =CH), 6.28 (br dd, J=10.3, 16.9 Hz, 1H, =CH), 5.73 (dd, J=1.6, 10.3 Hz, 1H, =CH). $^{13}$C (100 MHz, CDCl$_3$): δ=161.2 (C$_q$, CO), 137.8 (C$_q$), 129.4, 129.1 (=CH$_2$), 128.9, 126.3, 125.1 (C—Ar). MS (ESI): m/z 147 (M$^+$-O), 119, 93, 77.

N-(4-(dimethylamino)phenyl)-N-hydroxybenzamide

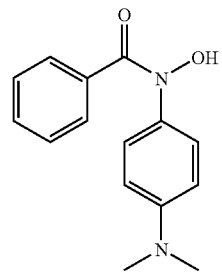

DBU (15 mg, 0.1 mmol) was added under argon to a solution of benzaldehyde (106 mg, 1 mmol), N,N-dimethyl-4-nitrosobenzenamine (150 mg, 1 mmol) and catalyst (36.4 mg, 0.1 mmol) in dichloromethane (5 mL). The reaction mixture was stirred at room temperature for 60 min. The solvent was removed under vacuum, and the residue was purified by flash silica gel column chromatography using hexane and ethyl acetate as the eluents.

$^1$H (400 MHz, CDCl$_3$): δ=7.86 (d, AB, J$_{AB}$=7.2 Hz, 2H), 7.65 (br s, 1H, OH), 7.55-7.46 (m, 5H, Ar—H), 6.75 (d, AB, J$_{AB}$=8.8 Hz, 2H), 2.95 (s, 6H, CH$_3$). $^{13}$C (100 MHz, CDCl$_3$): δ=165.5 (C$_q$, CO), 148.2 (C$_q$), 135.3 (C$_q$), 131.5, 128.7, 127.7 (C$_q$), 126.9, 122.0, 113.1, 40.9. MS (ESI): m/z 240 (M$^+$-O), 135, 121, 105, 77.

N-hydroxy-N-(4-hydroxy-3,5-dimethylphenyl)benzamide

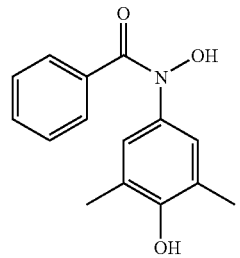

DBU (15 mg, 0.1 mmol) was added under argon to a solution of benzaldehyde (106 mg, 1 mmol), 2,6-dimethyl-4-nitrosophenol (151 mg, 1 mmol) and catalyst (36.4 mg, 0.1 mmol) in dichloromethane (5 mL). The reaction mixture was stirred at room temperature for 60 min. The solvent was removed under vacuum, and the residue was purified by flash silica gel column chromatography using hexane and ethyl acetate as the eluents.

$^1$H (400 MHz, CDCl$_3$): δ=7.43-7.42 (m, 2H, Ar—H), 7.36 (br s, 1H, OH), 7.34-7.32 (m, 3H, Ar—H), 7.26 (s, 2H, Ar—H), 2.26 (s, 6H, CH$_3$). $^{13}$C (100 MHz, CDCl$_3$): δ=165.6 (C$_q$, CO), 149.4 (C$_q$), 135.1 (C$_q$), 131.7, 130.1 (C$_q$), 128.8, 126.9, 123.7, 121.2, 16.1. MS (ESI): m/z 241 (M$^+$-O), 138, 105, 77.

N-(2,6-difluorophenyl)-N-hydroxybenzamide

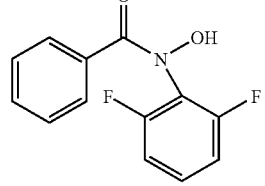

DBU (15 mg, 0.1 mmol) was added under argon to a solution of benzaldehyde (106 mg, 1 mmol), 1,3-difluoro-2-nitrosobenzene (143 mg, 1 mmol) and catalyst (36.4 mg, 0.1 mmol) in dichloromethane (5 mL). The reaction mixture was stirred at room temperature for 60 min. The solvent was removed under vacuum, and the residue was purified by flash silica gel column chromatography using hexane and ethyl acetate as the eluents.

$^1$H (400 MHz, CDCl$_3$): δ=8.80 (br s, 1H, OH), 7.55-7.51 (m, 2H, Ar—H), 7.43-7.29 (m, 4H, Ar—H), 6.94-6.90 (m, 2H, Ar—H). $^{13}$C (100 MHz, CDCl$_3$): δ=169.7 ($C_q$, CO), 160.1, 157.5 ($C_q$), 131.7, 128.3, 128.0 (C—Ar), 118.3 ($C_q$), 112.3, 112.1 (C—Ar). MS (ESI): m/z 233 (M$^+$-O), 105, 77. N-hydroxy-N-o-tolylbenzamide

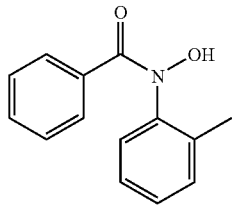

DBU (15 mg, 0.1 mmol) was added under argon to a solution of benzaldehyde (106 mg, 1 mmol), 1-methyl-2-nitrosobenzene (121 mg, 1 mmol) and catalyst (36.4 mg, 0.1 mmol) in dichloromethane (5 ml). The reaction mixture was stirred at room temperature for 60 min. The solvent was removed under vacuum, and the residue was purified by flash silica gel column chromatography using hexane and ethyl acetate as the eluents.

$^1$H (400 MHz, CDCl$_3$): δ=9.45 (br s, 1H, OH), 7.40-7.32 (m, 3H, Ar—H), 7.28-7.20 (m, 4H, Ar—H), 7.15-7.12 (m, 2H, Ar—H), 2.32 (s, 3H, CH$_3$). $^{13}$C (100 MHz, CDCl$_3$): δ=165.6 ($C_q$, CO), 138.1 ($C_q$), 136.9 ($C_q$), 131.4 ($C_q$), 131.3, 131.1, 130.0, 129.3, 128.6, 128.1, 126.9, 17.7. MS (ESI): m/z 211 (M$^+$-O), 105, 77.

In studies using different imidazolium and triazolium salts, it was observed that sterically less hindered triazolium salts provided higher yields of the product (Table 1).

Reaction with catalyst concentrations as low as 0.125 mol % was observed.

TABLE 1

Reaction Conditions for the Preparation of Hydroxamic Acids

| entry | catalyst (mol %) | | solvent | Base (mol %) | GC yield, % |
|---|---|---|---|---|---|
| 1 | [pyrrolidine-fused triazolium–C$_6$F$_5$, BF$_4^-$] | (20) | CH$_2$Cl$_2$ | DBU | 99 |
| 2 | [1,4-diphenyl-3-phenyl-triazolium, ClO$_4^-$] | (20) | CH$_2$Cl$_2$ | KO$^t$Bu | 50 |
| 3 | [1,3-diisopropylimidazolium, BF$_4^-$] | (20) | CH$_2$Cl$_2$ | KO$^t$Bu | Trace |
| 4 | [1,3-dimesitylimidazolium, X$^-$] | (20) | CH$_2$Cl$_2$ | KO$^t$Bu | 55 |

TABLE 1-continued

Reaction Conditions for the Preparation of Hydroxamic Acids

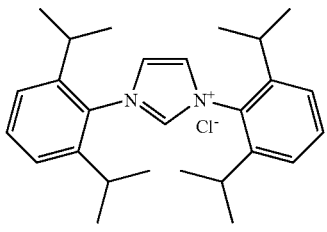

| entry | catalyst (mol %) | solvent | Base (mol %) | GC yield, % |
|---|---|---|---|---|
| 5 | 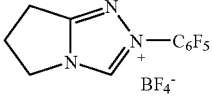 (20) | CH$_2$Cl$_2$ | KO$^t$Bu | Trace |
| 6 | 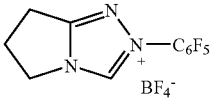 (20) | CH$_2$Cl$_2$ | KO$^t$Bu | 95 |
| 7 | 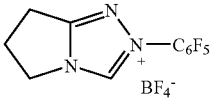 (20) | THF | KO$^t$Bu | 85 |
| 8 | 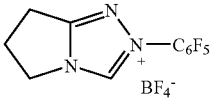 (5) | CH$_2$Cl$_2$ | DBU | 99 |
| 9 | 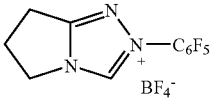 (0.5) | CH$_2$Cl$_2$ | DBU | 99 |
| 10 | none | CH$_2$Cl$_2$ | DBU | 0 |

Benzaldehyde and nitrosobenzene were observed to react in the presence of the NHC catalyst generated from the triazolium salt and DBU, forming N-hydroxy-N-phenylbenzamide in yields above 75%. No formation of benzoin was observed under these conditions (Table 2).

Yields above 75% of the corresponding hydroxamic acids for a variety of aryl, alkyl, alkenyl, and heterocyclic aldehydes were observed (Table 2).

Yields above 75% of the corresponding hydroxamic acids for a variety of nitroso compounds were observed (Table 2). Yields above 75% are considered excellent yields.

TABLE 2

Preparation of Hydroxamic Acids with Various Aldehydes or Nitroso Compounds

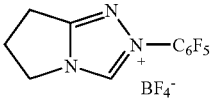

| entry | R$_1$ | R$_2$ | isolated yield, % |
|---|---|---|---|
| 1 | C$_6$H$_5$ | C$_6$H$_5$ | 96 |
| 2 | 4-OMeC$_6$H$_5$ | C$_6$H$_5$ | 99 |
| 3 | 4-NO$_2$C$_6$H$_5$ | C$_6$H$_5$ | 99 |
| 4 | 4-BrC$_6$H$_5$ | C$_6$H$_5$ | 95 |
| 5 | 1-methyl-1H-imidazol-2- | C$_6$H$_5$ | 98 |
| 6 | C$_6$H$_5$CH(CH$_3$) | C$_6$H$_5$ | 89 |
| 7 | C$_6$H$_5$CH$_2$CH$_2$ | C$_6$H$_5$ | 78 |

TABLE 2-continued

Preparation of Hydroxamic Acids with Various Aldehydes or Nitroso Compounds

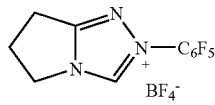

| entry | R₁ | R₂ | isolated yield, % |
|---|---|---|---|
| 8 | C₆H₁₁ | C₆H₅ | 97 |
| 9 | C₃H₅ | C₆H₅ | 99 |
| 10 | n-C₄H₉ | C₆H₅ | 99 |
| 11 | C₆H₅CH=CH | C₆H₅ | 95 |
| 12 | C₆H₅CH=C(CH₃) | C₆H₅ | 96 |
| 13 | 4-OMeC₆H₄CH=CH | C₆H₅ | 87 |
| 14 | 4-NO₂C₆H₄CH=CH | C₆H₅ | 99 |
| 15 | 3-OMe-4-OTfC₆H₄CH=CH | C₆H₅ | 80 |
| 16 | EtOOC—CH=CH | C₆H₅ | 99 |
| 17 | CH₂=CH | C₆H₅ | 99 |
| 18 | C₆H₅ | 4-(Me)₂NC₆H₅ | 93 |
| 19 | C₆H₅ | 3,5-Me-4-(OH)C₆H₅ | 55 |
| 20 | C₆H₅ | 2,6-F₂C₆H₅ | 82 |
| 21 | C₆H₅ | 2-MeC₆H₅ | 77 | catalyst:

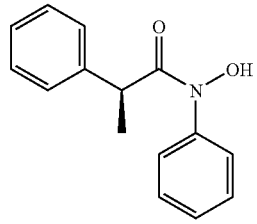

Azoxybenzene was observed as a side-product. By modifying the reaction conditions according to routine experiments, the amount of azoxybenzene can be minimized.

Procedure for NHC-Catalyzed Synthesis of Chiral Hydroxamic Acids

DBU (7.5 mg, 0.05 mmol) was added under argon to a solution of aldehyde (0.50 mmol), nitroso compound (0.51 mmol) and the catalyst (0.05 mmol) in dichloromethane (2 mL). The reaction mixture was stirred at room temperature for 3 h. The solvent was removed under vacuum, and the residue was purified by flash silica gel column chromatography using hexane and ethyl acetate as the eluents.

Procedure for NHC-Catalyzed Kinetic Resolution of α-Branched Aldehyde

KBu$^t$O (7.5 mg, 0.05 mmol) was added under argon to a solution of aldehyde (1 mmol), nitroso compound (0.50 mmol) and the catalyst (0.05 mmol) in dichloromethane (3 mL). The reaction mixture was stirred at room temperature for 3 h. The solvent was removed under vacuum, and the residue was purified by flash silica gel column chromatography using hexane and ethyl acetate as the eluents. The ee value was determined by chiral HPLC using OD-RH column (47% AcN/Water). The GC yields were determined by using dodecane as an internal standard.

N-hydroxy-N,2-diphenylpropanamide $^1$H (400 MHz, CDCl₃): δ=8.91 (br s, 1H₂OH), 7.42-7.39 (m, 3H, Ar—H), 7.28-7.21 (m, 5H, Ar—H), 7.15-7.10 (m, 2H, Ar—H), 3.72 (br s, 1H, CH), 1.50 (br s, J=7.0 Hz, 3H, CH₃). $^{13}$C (100 MHz, CDCl₃): δ=169.5 (C$_q$, CO), 140.7 (C$_q$), 138.1 (C$_q$), 129.5, 129.4, 128.7, 127.7, 127.4, 127.1, 41.9, 19.8. MS (ESI): m/z 225, 132, 120, 105, 93, 77.

The α-branched aldehyde and nitroso compound were observed to react in the presence of the NHC catalyst generated from the triazolium salt and 1,8-diazabicyclo[5.4.0]undec-7-ene (DBU), forming the R-enantiomer of the corresponding chiral hydroxamic acid in 90% yields.

The kinetic resolution of the α-branched aldehyde racemate was investigated by using different chiral triazolium salts. Yields of up to 50% of the corresponding chiral hydroxamic acids and moderate to good ee values (30-75%) were observed (Table 3).

TABLE 3

NHC-catalyzed Kinetic Resolution of α-Branched Aldehyde

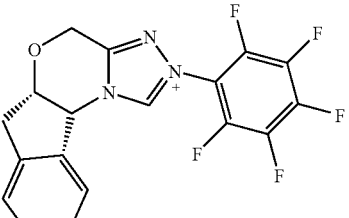

| Entry | Catalyst | Solvent | Yield | % ee |
|---|---|---|---|---|
| 1 | | CH₂Cl₂ | 50$^a$ | 75 |

TABLE 3-continued

NHC-catalyzed Kinetic Resolution of α-Branched Aldehyde

| Entry | Catalyst | Solvent | Yield | % ee |
|---|---|---|---|---|
| 2 | (pentafluorophenyl indano-oxazino-triazolium) | THF | 44[b] | 43 |
| 3 | (pentafluorophenyl indano-oxazino-triazolium) | THF + Toluene (1:9) | 50[b] | 45 |
| 4 | (pentafluorophenyl indano-oxazino-triazolium) | CH$_3$CN | 40[b] | 55 |
| 5 | (benzyl pyrrolo-triazolium C$_6$F$_5$) | CH$_2$Cl$_2$ | 50[b] | 30 |
| 6 | (2,6-dichloro-4-trifluoromethylphenyl indano-oxazino-triazolium) | CH$_2$Cl$_2$ | 45[b] | 30 |

[a]Isolated yield.
[b]GC yield

II. Process for Preparing N-Propionyloxyacrylamide Derivative

In an embodiment of the present invention, an aldehyde represented by the formula:

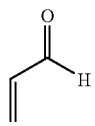

may be reacted in stoichiometric excess with a nitroso compound represented by the formula (III):

wherein $R_2$ may be defined as anywhere above, in the presence of a NHC catalyst to prepare a N-propionyloxyacrylamide derivative represented by the formula:

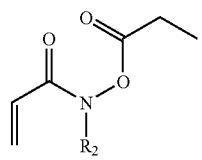

wherein $R_2$ may be defined as anywhere above.

In an embodiment of the present invention, the nitroso compound may be, for example, and without limitation, nitrosobenzene.

In an embodiment of the present invention, N-propionyloxy-N-phenylacrylamide represented by the following formula:

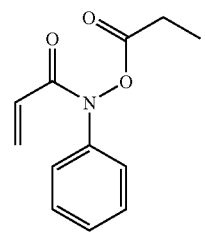

may be prepared.

Suitable amounts of the aldehyde would be understood to and can be determined by those of ordinary skill in the art. In an embodiment of the present invention, for example, and without limitation, the aldehyde may be reacted according to four times its stoichiometric ratio with the nitroso compound. In an embodiment of the present invention, for example, the aldehyde may be reacted according to three times its stoichiometric ratio with the nitroso compound.

Without being bound by theory, it is believed that in this aspect of the present invention, two catalytic cycles seem to operate. By way of example, and without limitation, as represented in the following scheme, it is believed that one catalytic cycle forms a hydroxamic acid 3 by the reaction of a $d^1$ nucleophile with the nitroso compound, and a second catalytic cycle forms N-propionyloxy-N-phenylacrylamide through protonation of a $d^3$ nucleophile, which forms an activated ester vii which then reacts with the hydroxamate nucleophile forming the product 7 and the carbene catalyst.

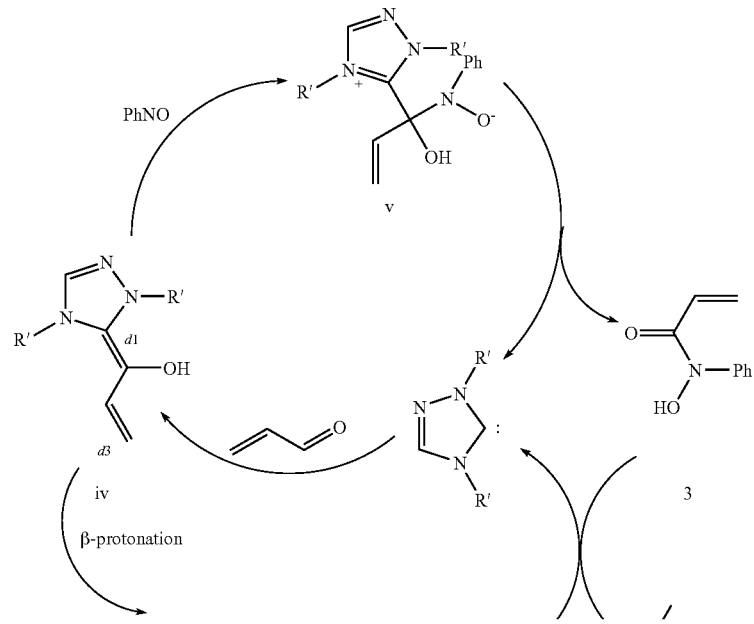

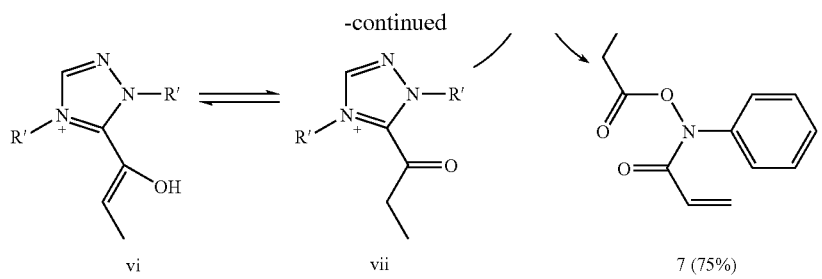

wherein R' is a hydrocarbon group including those as defined for $R_1$ above.

The skilled person will appreciate that the base, the solvent, the amount of the NHC catalyst, the reaction time, the reaction temperature, the isolation methods and the purification methods described above, which may be used for preparing the hydroxamic acid, may also be used for preparing the N-propionyloxyacrylamide derivative as described herein.

N-Propionyloxy-N-phenylacrylamide

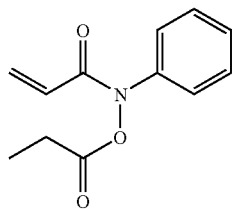

DBU (15 mg, 0.1 mmol) was added under argon to a solution of acrolein (168 mg, 3 mmol), nitrosobenzene (107 mg, 1 mmol) and catalyst (36.4 mg, 0.1 mmol) in dichloromethane (5 mL). The reaction mixture was stirred at room temperature for 10 min. The solvent was removed under vacuum, and the residue was purified by flash silica gel column chromatography using hexane and ethyl acetate as the eluents.

$^1$H (400 MHz, $CDCl_3$): δ=7.49-7.37 (m, 5H, Ar—H), 6.50 (d, J=16.6 Hz, 1H, =CH), 6.19 (br dd, J=10.5, 16.6 Hz, 1H, =CH), 5.70 (d, J=10.5 Hz, 1H, =CH), 2.51 (q, J=7.5 Hz, 2H, $CH_2$), 1.22 (t, J=7.5 Hz, 1H, $CH_3$). $^{13}$C (100 MHz, $CDCl_3$): δ=171.4, 162.2, 138.8, 129.7, 129.4, 129.3, 127.5, 126.6, 25.0, 8.7.

The present invention includes isomers such as geometrical isomers, optical isomers based on asymmetric carbon, stereoisomers and tautomers and is not limited by the description of the formula illustrated for the sake of convenience.

Although the foregoing invention has been described in some detail by way of illustration and example, and with regard to one or more embodiments, for the purposes of clarity of understanding, it is readily apparent to those of ordinary skill in the art in light of the teachings of this invention that certain changes, variations and modifications may be made thereto without departing from the spirit or scope of the invention as described in the appended claims.

It must be noted that as used in the specification and the appended claims, the singular forms of "a", "an" and "the" include plural reference unless the context clearly indicates otherwise.

Unless defined otherwise all technical and scientific terms used herein have the same meaning as commonly understood to one of ordinary skill in the art to which this invention belongs.

All publications, patents and patent applications cited in this specification are incorporated herein by reference as if each individual publication, patent or patent application were specifically and individually indicated to be incorporated by reference. The citation of any publication, patent or patent application in this specification is not an admission that the publication, patent or patent application is prior art.

The invention claimed is:

1. A process for preparing a hydroxamic acid represented by the formula (I):

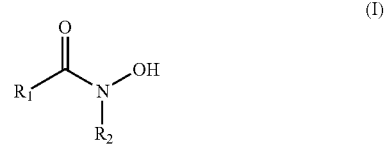

wherein:
$R_1$ is a hydrogen atom, a $C_{1-6}$ alkyl group which may be substituted with one or more sub stituents which are the same or different, a $C_{2-6}$ alkenyl group which may be substituted with one or more substituents which are the same or different, a $C_{2-6}$ alkynyl group which may be substituted with one or more substituents which are the same or different, a $C_{3-8}$ cycloalkyl group which may be substituted with one or more sub stituents which are the same or different, a $C_{3-8}$ cycloalkenyl group which may be substituted with one or more substituents which are the same or different, a $C_{6-14}$ aryl group which may be substituted with one or more substituents which are the same or different, a $C_{6-14}$ aryl-$C_{1-6}$ alkyl group which may be substituted with one or more substituents which are the same or different, a $C_{6-14}$ aryl-$C_{2-6}$ alkenyl group which may be substituted with one or more substituents which are the same or different, a $C_{6-14}$ aryl-$C_{2-6}$ alkynyl group which may be substituted with one or more substituents which may be the same or different, a 4- to 10-membered non-aromatic heterocyclic group containing one or more heteroatoms which are independently nitrogen, sulfur or oxygen and which group may be substituted with one or more substituents which are the same or different, or a 5- to 14-membered aromatic heterocyclic group containing one or more heteroatoms which are independently nitrogen, sulfur or oxygen and which group may be substituted with one or more substituents which are the same or different; and $R_2$ is a $C_{6-14}$ aryl group which may be substituted with one or more substituents which are the same or different, which process comprises reacting an aldehyde represented by the formula (II):

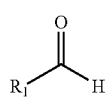

(II)

wherein R₁ is as defined above, with a nitroso compound represented by the formula (III):

(III)

wherein R₂ is as defined above, in the presence of a N-heterocyclic carbene (NHC) catalyst, the NHC catalyst being derived from a triazolium salt represented by the formula

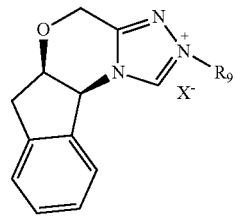

wherein R₉ is phenyl (Ph) which may be substituted, i-propyl ($^i$Pr), mesityl (Mes) or 2,6-diisopropylphenyl (2,6-$^i$Pr-Ph); and X⁻ is Br⁻, BF₄⁻ or CF⁻.

2. The process according to claim 1, wherein R₁ is a C₁₋₆ alkyl group, a C₂₋₆ alkenyl group which may be substituted with C₁₋₆ alkoxycarbonyl, a C₃₋₈ cycloalkyl group, a C₆₋₁₄ aryl group which may be substituted with C₁₋₆ alkoxy, nitro or halogen, a C₆₋₁₄ aryl-C₁₋₆ alkyl group, a C₆₋₁₄ aryl-C₂₋₆ alkenyl group, a C₆₋₁₄ aryl-C₂₋₆ alkenyl group wherein the C₆₋₁₄ aryl may be substituted with one or more substituents which are independently C₁₋₆ alkoxy, nitro or trifluoromethylsulfonyl, or a 5- to 14-membered aromatic heterocyclic group containing 1 to 4 heteroatoms which are independently nitrogen, oxygen or sulfur and which group may be substituted with C₁₋₆ alkyl; and R₂ is a phenyl group which may be substituted with one or more substituents, which are the same or different, and are a halogen atom, an amino group which may be substituted by C₁₋₆ alkyl, a C₁₋₆ alkyl group or a hydroxyl group.

3. A process for preparing a chiral hydroxamic acid represented by the formula (IV):

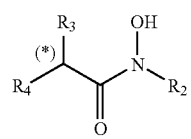

(IV)

wherein:
(*) refers to a chiral center;
R₂ is a C₆₋₁₄ aryl group which may be substituted with one or more substituents which are the same or different; and R₃ and R₄, which are different, is each a halogen atom, a hydroxyl group, a thiol group, a nitro group, a nitrile group, a cyano group; a C₁₋₆ alkyl, C₂₋₆ alkenyl or C₂₋₆ alkynyl group which may be substituted; a C₃₋₈ cycloalkyl or C₃₋₈ cycloalkenyl group which may be substituted; a C₆₋₁₄ aryl group which may be substituted, a C₆₋₁₄ aryl-C₁₋₆ alkyl group which may be substituted, a C₆₋₁₄ aryl-C₂₋₆ alkenyl group which may be substituted, a C₆₋₁₄ aryl-C₂₋₆ alkynyl group which may be substituted, a 4- to 10-membered non-aromatic heterocylic group containing 1 to 4 heteroatoms which are independently nitrogen, oxygen or sulfur and which group may be substituted, a 5- to 14-membered aromatic heterocylic group containing 1 to 4 heteroatoms which are independently nitrogen, oxygen or sulfur and which group may be substituted, a C₁₋₆ alkoxy group which may be substituted, a C₃₋₈ cycloalkoxy group which may be substituted; a C₁₋₆alkylthio, C₂₋₆ alkenylthio or C₂₋₆ alkynylthio group which may be substituted; a C₃₋₈ cycloalkylthio or C₃₋₈ cycloalkenylthio group which may be substituted; a C₆₋₁₄ aryloxy group which may be substituted, a 4- to 10-membered non-aromatic heterocycle-oxy group which may be substituted, a 5- to 14-membered aromatic heterocycle-oxy group which may be substituted, a C₆₋₁₄ arylthio group which may be substituted, a 4-to 10-membered non-aromatic heterocycle-thio group which may be substituted, a 5- to 14-membered aromatic heterocycle-thio group which may be substituted, an amino group which may be substituted, an azide group, a guanidino group, a carbamide group, a formyl group, a C₁₋₆imidoyl group, a carbonyl group which is substituted, a carbonyl-oxy group which is substituted, a carboxy group, a carbamoyl group which may be substituted, a C₁₋₄ alkylenedioxy group, a sulfanyl group, a sulfinyl group which is substituted, a sulfonyl group which is substituted, a C₁₋₆alkoxycarbonyl group, a C₁₋₆ alkylsulfonyl group, an oxo group or a C₁₋₆alkoxyimino group, which process comprises reacting a α-branched aldehyde represented by the formula (V):

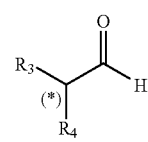

(V)

wherein R₃ and R₄ are as defined above, with a nitroso compound represented by the formula (III):

(III)

wherein R₂ is as defined above, in the presence of a N-heterocyclic carbene (NHC) catalyst, the NHC catalyst being derived from a triazolium salt represented by the formula

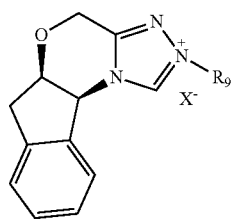

wherein R$_9$ is phenyl (Ph) which may be substituted, i-propyl ($^i$Pr), mesityl (Mes) or 2,6-diisopropylphenyl (2,6-$^i$Pr-Ph); and X$^-$ is Br$^-$, BF$_4^-$ or Cl$^-$.

4. The process according to claim 3, wherein R$_3$ is a C$_{1-6}$ alkyl group; and R$_4$ is a phenyl group.

5. The process according to claim 3, the chiral hydroxamic acid is prepared in enantiomeric excess.

6. The process according to claim 3, wherein the α-branched aldehyde is a racemate.

7. The process according to claim 3, wherein a stoichiometric excess of the α-branched aldehyde is reacted.

8. The process according to claim 3, wherein the reaction is stopped at about 50% conversion of the α-branched aldehyde.

9. The process according to claim 1, wherein the reaction is carried out in the presence of a base that is 1,8-diazabicyclo[5.4.0]undec-7-ene or potassium tert-butoxide and in the presence of a solvent that is dichloromethane or tetrahydrofuran.

10. The process according to claim 3, wherein the reaction is carried out in the presence of a base that is 1,8-diazabicyclo[5.4.0]undec-7-ene or potassium tert-butoxide and in the presence of a solvent that is dichloromethane or tetrahydrofuran.

11. A process for preparing a hydroxamic acid represented by the formula (I):

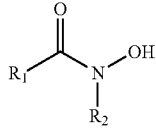
(I)

wherein R$_1$ a C$_{1-6}$ alkyl group substituted with phenyl and R$_2$ is phenyl;
which process comprises reacting an aldehyde represented by the formula (II):

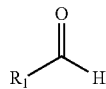
(II)

wherein R$_1$ is as defined above, with a nitroso compound represented by the formula (III):

(III)

wherein R$_2$ is as defined above, in the presence of the following N-heterocyclic carbene (NHC) catalyst:

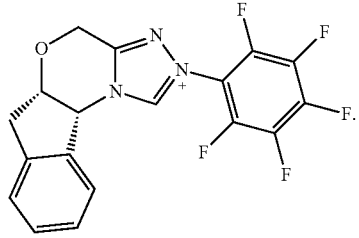

12. The process according to claim 11, wherein R$_1$ is 1-phenylethyl.

13. The process according to claim 11, wherein the reaction is carried out in the presence of a base that is 1,8-diazabicyclo[5.4.0]undec-7-ene or potassium tert-butoxide and in the presence of a solvent that is dichloromethane or tetrahydrofuran.

14. The process according to claim 11 for preparing a chiral hydroxamic acid represented by the formula (IV):

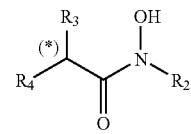
(IV)

wherein:
(*) refers to a chiral center; R$_2$ is phenyl; and R$_3$ and R$_4$, which are different, is each phenyl and a C$_{1-5}$ alkyl;
which process comprises reacting a α-branched aldehyde represented by the formula (V):

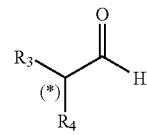
(V)

wherein R$_3$ and R$_4$ are as defined above, with a nitroso compound represented by the formula (III):

(III)

wherein R$_2$ is as defined above, in the presence of the NHC catalyst.

15. The process according to claim 14, wherein R$_3$ is a methyl group; and R$_4$ is a phenyl group.

16. The process according to claim 14, wherein the chiral hydroxamic acid is prepared in enantiomeric excess.

17. The process according to claim 14, wherein the α-branched aldehyde is a racemate.

18. The process according to claim 14, wherein a stoichiometric excess of the α-branched aldehyde is reacted.

19. The process according to claim 14, wherein the reaction is stopped at about 50% conversion of the α-branched aldehyde.

20. The process according to claim 14, wherein the reaction is carried out in the presence of a base that is 1,8-diazabicyclo[5.4.0]undec-7-ene or potassium tert-butoxide and in the presence of a solvent that is dichloromethane or tetrahydrofuran.

* * * * *